US011129885B2

(12) United States Patent
Luo et al.

(10) Patent No.: US 11,129,885 B2
(45) Date of Patent: Sep. 28, 2021

(54) VIRUS LIKE PARTICLE OF HEPATITIS B VIRUS PRE-S PROTEIN

(71) Applicants: Georgia State University Research Foundation, Inc., Atlanta, GA (US); Peking University, Beijing Shi (CN)

(72) Inventors: Ming Luo, Atlanta, GA (US); Xiaodan Cai, Beijing Shi (CN)

(73) Assignees: Georgia State University Research Foundation, Inc., Atlanta, GA (US); Peking University, Beijing (CN)

( * ) Notice: Subject to any disclaimer, the term of this patent is extended or adjusted under 35 U.S.C. 154(b) by 43 days.

(21) Appl. No.: 16/346,161

(22) PCT Filed: Oct. 19, 2017

(86) PCT No.: PCT/US2017/057390
§ 371 (c)(1),
(2) Date: Apr. 30, 2019

(87) PCT Pub. No.: WO2018/080889
PCT Pub. Date: May 3, 2018

(65) Prior Publication Data
US 2020/0046824 A1 Feb. 13, 2020

Related U.S. Application Data

(60) Provisional application No. 62/414,899, filed on Oct. 31, 2016.

(51) Int. Cl.
*A61K 39/12* (2006.01)
*A61P 31/12* (2006.01)
*A61K 39/00* (2006.01)

(52) U.S. Cl.
CPC .............. *A61K 39/12* (2013.01); *A61P 31/12* (2018.01); *A61K 2039/5258* (2013.01); *A61K 2039/545* (2013.01); *A61K 2039/55505* (2013.01)

(58) Field of Classification Search
CPC ............ A61K 39/12; A61K 2039/5258; A61K 2039/545; A61K 2039/55505; A61P 31/12; A61P 43/00; C12N 2730/10123; C12N 2730/10134
See application file for complete search history.

(56) References Cited

U.S. PATENT DOCUMENTS

| | | | | |
|---|---|---|---|---|
| 2005/0186621 A1* | 8/2005 | Galarza | ................ | C07K 14/005 435/5 |
| 2011/0257080 A1 | 10/2011 | Chai et al. | | |
| 2015/0024038 A1* | 1/2015 | Fischer | ................ | A61K 39/092 424/450 |
| 2015/0273048 A1 | 10/2015 | Kang et al. | | |

FOREIGN PATENT DOCUMENTS

| | | | |
|---|---|---|---|
| CN | 106928372 A | * | 7/2017 |
| CN | 106928372 A | | 7/2017 |
| WO | 2006045532 A2 | | 5/2006 |
| WO | 2012168487 A1 | | 12/2012 |

OTHER PUBLICATIONS

Chen BF. Hepatitis B virus pre-S/S variants in liver diseases. World J Gastroenterol. Apr. 14, 2018;24(14):1507-1520.;.*
Chai N, Gudima S, Chang J, Taylor J. Immunoadhesins containing pre-S domains of hepatitis B virus large envelope protein are secreted and inhibit virus infection. J Virol. May 2007;81(10):4912-8. Epub Feb. 28, 2007.*
Roose K, De Baets S, Schepens B, Saelens X. Hepatitis B core-based virus-like particles to present heterologous epitopes. Expert Rev Vaccines. Feb. 2013;12(2):183-98.*
Yum JS, Ahn BC, Jo HJ, Kim DY, Kim KH, Kim HS, Sung YC, Yoon J, Morrey J, Moon HM. Use of pre-S protein-containing hepatitis B virus surface antigens and a powerful adjuvant to develop an immune therapy for chronic hepatitis B virus infection. Clin Vaccine Immunol. Feb. 2012;19(2): 120-7. Epub Dec. 7, 2011.*
Neirynck S, Deroo T, Saelens X, Vanlandschoot P, Jou WM, Fiers W. A universal influenza A vaccine based on the extracellular domain of the M2 protein. Nat Med. Oct. 1999;5(10):1157-63.*
English Machine translation of CN106928372B, Dec. 30, 2016. Translation performed Jan. 26, 2021.*
Written translation of claims 1-5 CN106928372B, Dec. 30, 2016. Translation performed Jan. 25, 2021.*
Search Report issued from the European Patent Office for application 17863331.9, dated Apr. 30, 2020.
Shouval et al., Enhanced immune response to hepatitis B vaccination through immunization with a Pre-S1/Pre-S2/2 Vaccine, Med Microbiol Immunol, 204:57-68, 2015.
Noh et al., Chimeric Bivalent Virus-Like Particle Vaccine for H5N1 HPAI and ND Confers Protection against a Lethal Challenge in Chickens and Allows a Strategy of Differentiating Infected from Vaccinated Animals (DIVA), PLOS One, 1-13, 2016.
Cai et al., A virus-like particle of the hepatitis B virus preS antigen elicits robust neutralizing antibodies and T Cell responses in mice, Antiviral Research vol. 149. p. 48-57, 2017.

(Continued)

Primary Examiner — Rachel B Gill
(74) Attorney, Agent, or Firm — Thomas|Horstemeyer LLP

(57) ABSTRACT

As disclosed herein, the preS antigen on infectious hepatitis B virus (HBV) particles can provide B and T ceil epitopes that promote the humoral and cellular responses and enhance the seroprotection rate by overcoming non-responsiveness to the S antigen-only vaccines. Therefore, compositions and methods are disclosed using the preS antigen to develop vaccines and immune therapies for treating or preventing hepatitis B infection, in particular, virus-like particles (VLPs) are disclosed that contain the preS antigen on its surface. These VLPs can be used alone or in combination with vaccines containing the hepatitis B surface antigen (HBsAg) to vaccinate subjects against HBV as well as to activate T ceils for adoptive T cell therapy to eradicate HBV infected hapatocytes.

13 Claims, 20 Drawing Sheets
Specification includes a Sequence Listing.

(56) References Cited

OTHER PUBLICATIONS

Galarza et al., Virus-Like Particle (VLP) Vaccine Conferred Complete Protection against a Lethal Influenza Virus Challenge, Viral Immunology, vol. 18, No. 2, p. 244-251, 2005.
International Search Report issued for PCT/US2017/057390, dated Jan. 19, 2019.

* cited by examiner

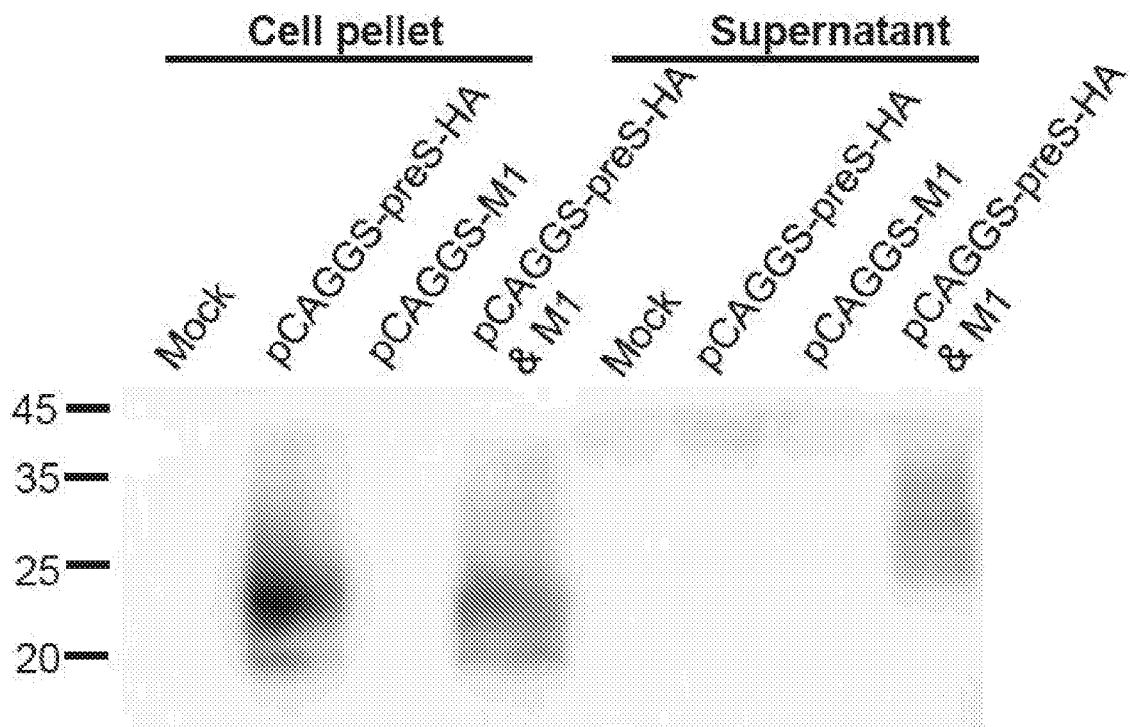
FIG. 2A
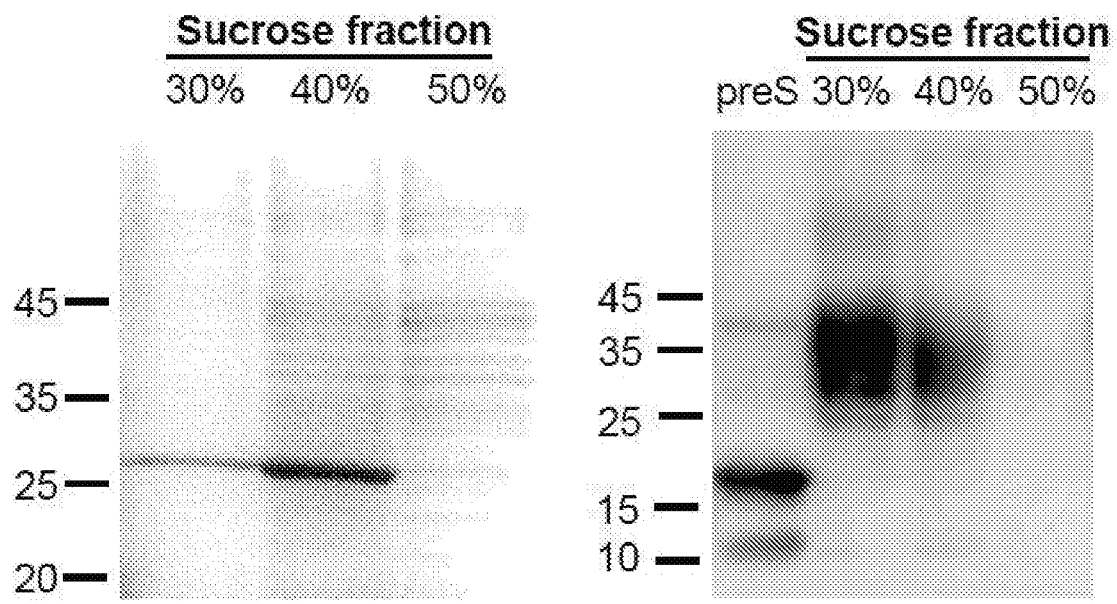
FIG. 2B
FIG. 2C

MEAKLFVLFCAFTALKAMGTNLSVPNPLGFFP
DHQLDPAFGANSNNPDWDFNPIKDHWPAANQ
VGVGAFGPGLTPPHGGILGWSPQAQGILTTVST
IPPPASTNRQSGRQPTPISPPLRDSHPQAMQW
NSTAFHQALQDPRVRGLYLPAGGSSSGTVNPA
PNIASHISSISARTGDPVTNKLESVGVHQILAIYS
TVASSLVLLVSLGAISFWMCSNGSLQCRICI

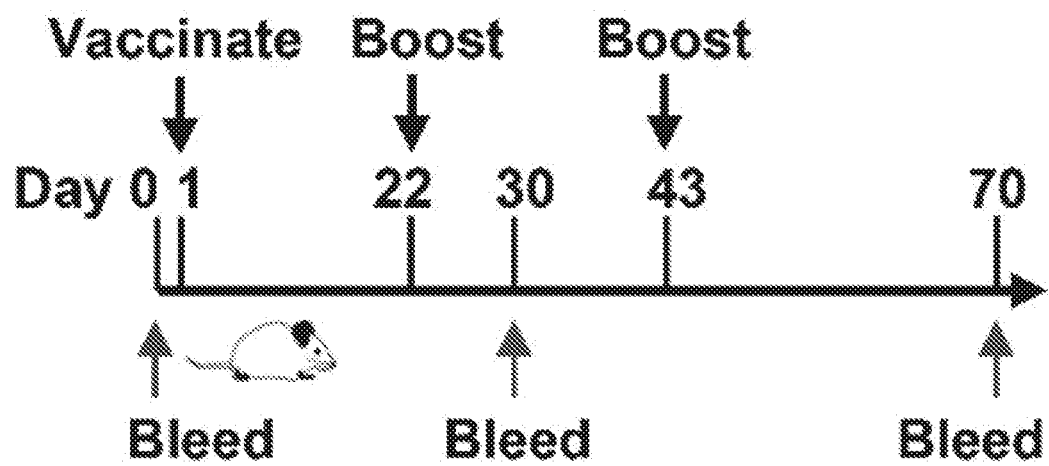
FIG. 7A
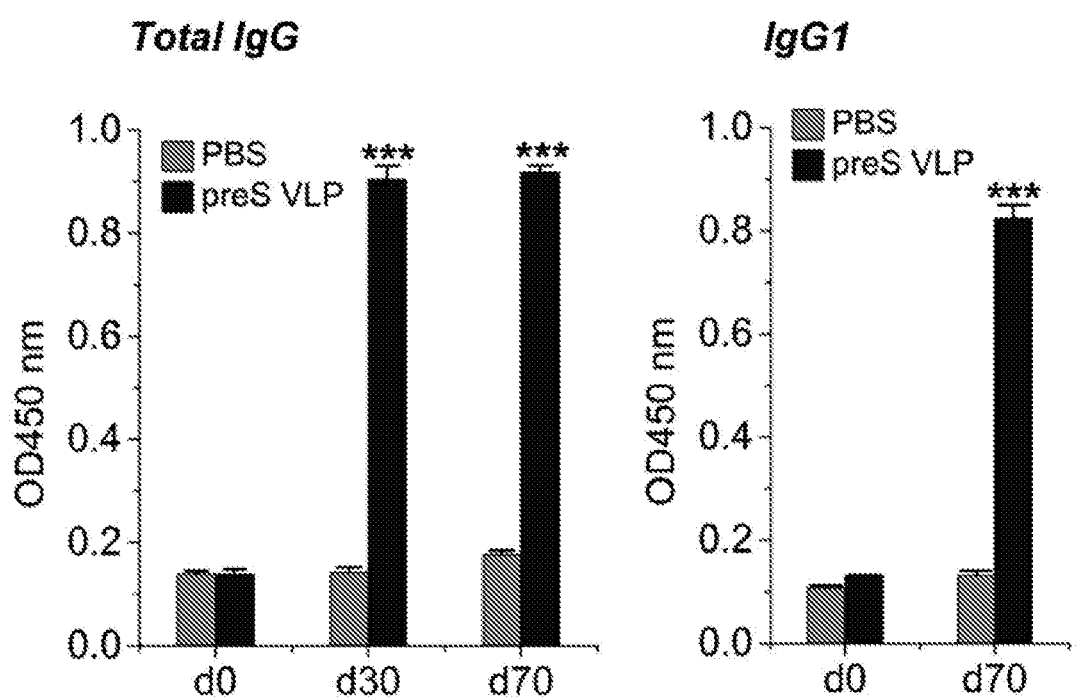
FIG. 7B
FIG. 7C

VIRUS LIKE PARTICLE OF HEPATITIS B VIRUS PRE-S PROTEIN

CROSS-REFERENCE TO RELATED APPLICATIONS

This application claims benefit of U.S. Provisional Application No. 62/414,899, filed Oct. 31, 2016, which is hereby incorporated herein by reference in its entirety.

BACKGROUND

Despite great progress in antiviral treatments, hepatitis B virus (HBV) infection is still a major global public health problem. Approximately 2 billion people have been infected worldwide during their lifetime, and more than 350 million are chronic carriers of the virus (Liaw Y F, et al. Lancet 2009 373:582-592). HBV infection may cause acute and chronic hepatitis, which leads to liver cirrhosis (LC) and hepatocellular carcinoma (HCC) (Chu C M. J Gastroenterol Hepatol 2000 15 Suppl:E25-30). Current HBV vaccines on the market which protect most people against HBV infection contain only the S antigen. However, almost 5-10% people vaccinated with the available vaccines fail to mount an adequate antibody response to offer protection (Kubba A K, et al. Commun Dis Public Health 2003 6:106-112).

SUMMARY

As disclosed herein, the HBV preS protein, or an antigenic fragment thereof, can provide B and T cell epitopes that promote the humoral and cellular responses and enhance the seroprotection rate by overcoming non-responsiveness to the S antigen-only vaccines. Therefore, compositions and methods are disclosed using a preS antigen to develop vaccines and immune therapies for treating or preventing hepatitis B infection.

In some embodiments, a preS antigen is incorporated into a virus-like particle (VLP) that can be used, for example, as a vaccine or to active T cells for adoptive cell transfer. In these embodiments, the preS antigen can be incorporated into a fusion protein that will incorporate into a VLP. For example, a fusion protein is disclosed that comprises a hepatitis B preS antigen fused at the N-terminus to a transmembrane domain and optional cytoplasmic tail of a viral envelope protein. Viral envelope proteins that contain transmembrane domains suitable for VLP formation include influenza virus hemagglutinin (HA) protein, a type I transmembrane protein. The hepatitis B preS antigen may also be fused with other type I transmembrane glycoproteins, such as glycoproteins from arenaviruses, bunyaviruses, coronaviruses, filoviruses, paramyxoviruses, retroviruses, togaviruses, and others (Liu J, et al. VIROLOGICA SINICA 2016 31 (4): 279-287).

In some embodiments, the fusion protein further contains a signal peptide at the N-terminus. As an example, the signal peptide can be the signal peptide from HA. The signal peptide may also be derived from other type I transmembrane glycoproteins, such as glycoproteins from arenaviruses, bunyaviruses, coronaviruses, filoviruses, paramyxoviruses, retroviruses, togaviruses, and others (Liu J, et al. VIROLOGICA SINICA 2016 31 (4): 279-287).

The fusion protein can be formed into a VLP by co-expressing it with a viral matrix protein, such as influenza virus matrix protein 1 (M1). The fusion protein can also be formed into a VLP by co-expressing it with other viral proteins, including matrix protein, nucleocapsid protein, and other proteins from arenaviruses, bunyaviruses, coronaviruses, filoviruses, paramyxoviruses, retroviruses, togaviruses, and others (Liu J, et al. VIROLOGICA SINICA 2016 31 (4): 279-287). Therefore, also disclosed are VLPs comprising the disclosed fusion protein and an influenza virus M1 protein. These VLPs can be produced, for example, by introducing expression vectors into mammalian cells (e.g. Chinese hamster ovary (CHO), human cell line 293, and Vero cells (money cells)) as transient or stable expression, or coinfecting insect cells with one or more recombinant baculoviruses expressing the M1 protein and the disclosed fusion protein, culturing the cells under appropriate conditions. VLPs can also be produced by the same methods when other viral proteins are employed in constructing the fusion protein and coexpression. The VLPs can then be purified from cell culture supernatants.

Also disclosed are vaccines comprising an effective amount of the disclosed VLPs in a pharmaceutically acceptable excipient. In some cases, the vaccine further comprises an adjuvant. For example, the adjuvant can be selected from the group consisting of AS04 (alum plus monophosphoryl lipid A), bacterial cell wall components, MF59 (mineral oil based adjuvant), and a molecular adjuvant incorporated VLP in a membrane-anchored form.

Also disclosed is an isolated polynucleotide comprising a nucleic acid sequence encoding the disclosed fusion protein can be constructed following the amino acid codons. In some embodiments, the nucleic acid sequence encoding the fusion protein is operably linked to an expression control sequence. Therefore, also disclosed is an expression vector comprising the disclosed nucleic acid sequence. Also disclosed herein is a cell comprising the disclosed vector. For example, the cell can be a bacterium, insect cell, mammalian cell or yeast cell.

Also disclosed is a method of vaccinating a subject for hepatitis B comprising administering a vaccine disclosed herein to a subject in need thereof by intranasal, intramuscular, subcutaneous, transdermal, or sublingual administration. The method can further involve administering to the subject a vaccine comprising the hepatitis B surface antigen (HBsAg).

Also disclosed is a method for activating CD8+ T cells for adoptive cell transfer (ACT), comprising co-culturing CD8+ T cells and dendritic cells with a VLPs disclosed herein.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic representation of pCAGGS-preS-HA and pCAGGS-M1 used for preS VLP production, and pET28b-preS used for the expression of preS antigen. FIG. 1B shows results of qPCR analyses used to measure the transcription of preS-HA and M1. FIGS. 1C and 1D are immunofluorescent images of preS-HA expressing cells. 293T cells were transfected with mock control, pCAGGS-M1, pCAGGS-preS-HA, or both plasmids. Cells either were (FIG. 1D) or were not (FIG. 1C) permeabilized with Triton X-100 before staining. The nuclei were stained with DAPI, and the preS antigen was stained with an anti-preS sera, detected with Alexa Fluor® 488-Conjugated goat anti-rabbit secondary antibody.

FIGS. 2A to 2E shows characterization of preS VLP. FIG. 2A shows Western blot analysis of preS-HA in lysates of plasmid transfected cells and cognate supernatant. FIG. 2B shows SDS-PAGE analysis of samples from fractions from sucrose gradient centrifugation. The major protein component is in the 40% sucrose fraction. FIG. 2C shows Western blot analysis with anti-preS sera. Lane 1 was for recombinant preS protein expressed in E. coli. Lanes 2 and 3 showed the presence of the preS-HA antigen in fractions from sucrose gradient centrifugation. FIG. 2D is an electron micrograph showing preS virus-like particles (preS VLP). Magnification, 11,000×. FIG. 2E LC-MS/MS identification of M1 and preS-HA in the sample from 40% sucrose fraction. Sequence shown is SEQ ID NO:2.

FIGS. 3A to 3C show serum anti-preS titers determined by ELISA. The plates were coated with 5 µg/mL recombinant preS. The immunization condition is labeled next to chart codes. The sera were diluted by 100 fold in all the assays. FIG. 3D shows neutralization of HBV infectivity in HepG2/hNTCP cells by mouse anti-preS VLP sera or hepatitis B immunoglobulin (HBIG) (0.144 mg/mL). The mouse anti-preS VLP sera were diluted by 10 folds. HBeAg values at one week post infection were measured using an ELISA kit. The data are represented as mean±SEM.

FIG. 5A shows liver-associated HBV RNA copies measured by qPCR. FIG. 5B shows immunohistochemistry analyses of liver tissues. Magnification, 100×. FIGS. 5C to 5E show serum analysis for HBsAg (FIG. 5C), HBeAg (FIG. 5D) and anti-preS antibody titers (FIG. 5E) completed by ELISA on days 0, 2, 4, and 7 post-challenge. FIG. 5F shows the serum alanine aminotransferase (ALT) activity that was determined with a Hitachi 7600 Automatic Biochemistry Analyzer. All values are presented as the average from each group, and error bars indicate ±SEM.

FIGS. 7A to 7J show immunization with preS VLP induces robust anti-preS antibodies and T cell responses in HBV transgenic mice. HBV transgenic mice were immunized intramuscularly with preS VLP (n=6) or PBS (n=6). FIG. 7A is a time schedule for preS VLP as a vaccine to treat HBV transgenic mice. FIGS. 7B to 7D show serum anti-preS titers determined by ELISA. The plates were coated with 1 µg/mL purified recombinant preS. The immunization condition is labeled next to chart color codes. The sera were diluted by 100 folds in all the assays. CD8+ T cells (FIG. 7E) or CD4+ T cells (FIG. 7F) were gated, and IFN-γ-producing cells are presented as the percent average from each group. FIG. 7G shows IFN-γ expression by ELISPOT assays in splenocytes isolated on day 70. ELISPOT experiments were performed in triplicate wells per condition. FIG. 7H shows representative images of ELISPOT from each group. All values are presented as the average from each group, and error bars indicate ±SEM. FIG. 7I shows the Serum alanine aminotransferase (ALT) activity that was measured using a Hitachi 7600 Automatic Biochemistry Analyzer. FIG. 7J shows liver tissue sections from each group that were stained with hematoxylin and eosin. Magnification, 100×.

DETAILED DESCRIPTION

Definitions

Figure 1A:
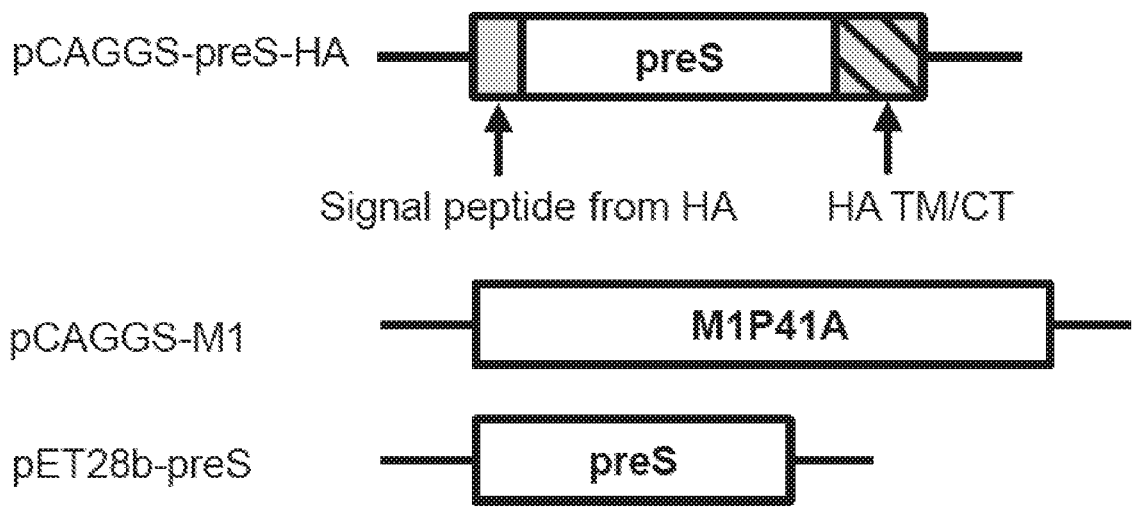
FIGS. 1A to 1D show construction and expression of preS VLP.

It must be noted that as used herein and in the appended claims, the singular forms "a," "an," and "the" include plural referents unless the context clearly dictates otherwise. Thus, for example, reference to "a peptide" includes a plurality of such peptides, reference to "the peptide" is a reference to one or more peptides and equivalents thereof known to those skilled in the art, and so forth.

In this specification and in the claims that follow, reference will be made to a number of terms that shall be defined to have the following meanings:

"Optional" or "optionally" means that the subsequently described event or circumstance can or cannot occur, and that the description includes instances where the event or circumstance occurs and instances where it does not. For example, the phrase "optionally a signal peptide" means that the signal peptide may or may not be included.

The term "universal influenza A vaccine" refers to vaccine capable of providing cross-protection against at least two, including three, four, five or more, subtypes of influenza A.

The term "individual," "host," "subject," and "patient" are used interchangeably to refer to any individual who is the target of administration, treatment, or vaccination. The subject can be a vertebrate, for example, a mammal. Thus, the subject can be a human or veterinary patient.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The terms "peptide," "protein," and "polypeptide" are used interchangeably to refer to a natural or synthetic molecule comprising two or more amino acids linked by the carboxyl group of one amino acid to the alpha amino group of another.

The term "protein domain" refers to a portion of a protein, portions of a protein, or an entire protein showing structural integrity; this determination may be based on amino acid composition of a portion of a protein, portions of a protein, or the entire protein.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "variant" refers to an amino acid sequence having conservative amino acid substitutions, non-conservative amino acid substitutions (i.e. a degenerate variant), or a peptide having 60%, 65%, 70%, 71%, 72%, 73%, 74%, 75%, 76%, 77%, 78%, 79%, 80%, 81%, 82%$, 83%, 84%, 85%, 86%, 87%, 88%, 89%, 90%, 91%, 92%, 93%, 94%, 95%, 96%, 97%, 98%, or 99% sequence identity to the recited sequence.

The term "percent (%) sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods. For purposes herein, the % sequence identity of a given nucleotides or amino acids sequence C to, with, or against a given nucleic acid sequence D (which can alternatively be phrased as a given sequence C that has or comprises a certain sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the sequence identity of C to D will not equal the % sequence identity of D to C.

A "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

A "spacer" as used herein refers to a peptide that joins the proteins of a fusion protein. Generally a spacer has no specific biological activity other than to join the proteins or to preserve some minimum distance or other spatial relationship between them. However, the constituent amino acids of a spacer may be selected to influence some property of the molecule, such as the folding, net charge, or hydrophobicity of the molecule.

Hepatitis B preS Constructs

Disclosed herein is a fusion protein comprising a heptatis B preS epitope fused to a membrane anchor domain, such as a transmembrane domain and optional cytoplasmic domain of a viral envelope protein, for use in producing virus-like particles.

For example, the heptatis B preS epitope sequences can be derived from human. In some embodiments, the hepatitis B preS antigen has the amino acid sequence MGT NLSVPN-PLGF FPDHQLDPAF GANSNNPDWD FNPIKDHWPA ANQVGVGAFG PGLTPPHGGI LGWSPQAQGI LTTVS-TIPPP ASTNRQSGRQ PTPISPPLRD SHPQAMQWNS TAFHQALQDP RVRGLYLPAG GSSSGTVNPA PNIASH-ISSI SARTGDPVTN (SEQ ID NO:1), or a conservative variant thereof having at least about 70%, 75%, 80%, 85%, 90%, 91%, 92%, 93%, 94%, 95%, 96%, 97%, 98%, 98%, 99%, or 100% sequence identity to SEQ ID NO:1 (e.g. 1, 2, 3, 4, 5, 6, 7, 8, 9, or 10 conservative amino acid substitutions).

The hepatitis B virus preS antigen from other genotypes or subtypes can also be used to produce VLPs by the same methods.

In some embodiments, the influenza virus M1 protein has the amino acid sequence MSLLTEVETY VLSIIPSGPL KAEIAQRLEG VFAGKNTDLE ALMEWLKTRP ILSPLTKGIL GFVFTLTVPS ERGLQRRRFV QNALNG-NGDP NNMDRAVKLY KKLKREITFH GAKEVSLSYS TGALASCMGL IYNRMGTVTT EAAFGLVCAT CEQIADSQHR SHRQMATTTN PLIRHENRMV LAST-TAKAME QMAGSSEQAA EAMEVASQTR QMVHAMRTIG THPSSSAGLK DDLLENLQAY QKRMGVQIQR FK (SEQ ID NO:3), or a conservative variant thereof having at least about 70%, 75%, 80%, 85%, 90%, 91%, 92%, 93%, 94%, 95%, 96%, 97%, 98%, 98%, 99%, or 100% sequence identity to SEQ ID NO:3 (e.g. 1, 2, 3, 4, 5, 6, 7, 8, 9, or 10 conservative amino acid substitutions).

The transmembrane-cytoplasmic domain from hemagglutinin can have the amino acid sequence KLESVGVHQI LAIYSTVASS LVLLVSLGAI SFWMCSNGSL QCRICI (SEQ ID NO:15), or a conservative variant thereof having at least 70%, 75%, 80%, 85%, 90%, 91%, 92%, 93%, 94%, 95%, 96%, 97%, 98%, 98%, 99%, or 100% sequence identity to SEQ ID NO:15.

The fusion protein may further comprise a signal peptide at the N-terminus to facilitate secretion. For example, the fusion protein may contain a hemagglutinin (HA) signal peptide. The signal peptide from hemagglutinin can have the amino acid sequence MEAKLFVLFC AFTALKA (SEQ ID NO:16), or a conservative variant thereof having at least 70%, 75%, 80%, 85%, 90%, 91%, 92%, 93%, 94%, 95%, 96%, 97%, 98%, 98%, 99%, or 100% sequence identity to SEQ ID NO:16. Other signal peptides are known and include those listed in Table 1 below.

TABLE 1

Signal Peptides

| Accession Number | Signal Sequence | SEQ ID NO |
|---|---|---|
| Q6DQ15 | VLLLAIVSLVKS | SEQ ID NO: 17 |
| P16060 | MERIVIALAIISVVKG | SEQ ID NO: 18 |

TABLE 1-continued

Signal Peptides

| Accession Number | Signal Sequence | SEQ ID NO |
|---|---|---|
| P03446 | MEKFIILSTVLAASFAY | SEQ ID NO: 19 |
| Q6LEJ4 | MNTQILVFIACVLIEAKG | SEQ ID NO: 20 |
| P09344 | MNTQILILTLVAAIHTNA | SEQ ID NO: 21 |
| P16561 | MARLPILLLLISLVYS | SEQ ID NO: 22 |
| P03459 | MNTQILVFALVAVIPTNA | SEQ ID NO: 23 |
| P03436 | MKTIIALSYIFCLALG | SEQ ID NO: 24 |
| P03445 | MKKVLLFAAIIICIRA | SEQ ID NO: 25 |
| Q82559 | MKTTIILILLTHWVYS | SEQ ID NO: 26 |
| P16996 | MKTTIVLILITHWVYS | SEQ ID NO: 27 |
| Q67371 | MKAIIVLLMVVTSNA | SEQ ID NO: 28 |
| Q80A30 | SLVKS | SEQ ID NO: 29 |
| P04659 | MEKTLLFAAIFLCVKA | SEQ ID NO: 30 |
| Q1PUD9 | MKTIIALSYIFCLVLG | SEQ ID NO: 31 |
| P26138 | MKTIIVLSCFFCLAFS | SEQ ID NO: 32 |
| P13102 | MDIRPIIISLLISTCVQA | SEQ ID NO: 33 |
| P10448 | LMVVTSNA | SEQ ID NO: 34 |
| P12443 | IVLLMVVTSNA | SEQ ID NO: 35 |
| Q6DQ18 | AIVSLVKS | SEQ ID NO: 36 |
| P26097 | MNTQILILATSAFLCVRA | SEQ ID NO: 37 |
| P03443 | MLSITILFLLIAEGSS | SEQ ID NO: 38 |
| Q9WCE3 | MEAKLLVLFCTFAALKA | SEQ ID NO: 39 |
| P08714 | MTRLPILLLLISLVYA | SEQ ID NO: 40 |
| P19696 | MLSIVILFLLIAENSS | SEQ ID NO: 41 |
| P16994 | MKTTIILILLIHWVHS | SEQ ID NO: 42 |
| Q03909 | MLSLIMRTVIALSYIFCLAFG | SEQ ID NO: 43 |
| Q60Q19 | MEKIVLLLAIVSLVKS | SEQ ID NO: 44 |
| P17002 | MKTTTILILTHWVHS | SEQ ID NO: 45 |
| P18875 | MKAKLLVLLCALSATDA | SEQ ID NO: 46 |
| P03451 | MAIIYLILLFTAVRG | SEQ ID NO: 47 |
| P26100 | MNTQILILAISAFLCVRA | SEQ ID NO: 48 |
| P11132 | MEEIVLLFAIVSLARS | SEQ ID NO: 49 |
| O89746 | MEKIVLLLATVSLVKS | SEQ ID NO: 50 |
| P03454 | MKAKLLVLLYAFVATDA | SEQ ID NO: 51 |
| Q0A3Y1 | MDIRAIVISLLISTCVQA | SEQ ID NO: 52 |
| P87506 | MERIVIALAIINIVKG | SEQ ID NO: 53 |
| P26562 | MEAKLFVLFCTFTVLKA | SEQ ID NO: 54 |
| P12583 | MKTIIALSYIFCLAFS | SEQ ID NO: 55 |
| P12590 | MKAKLLVLLCAFTATDA | SEQ ID NO: 56 |
| P33807 | MTRLSILLLLISLVYS | SEQ ID NO: 57 |
| Q9WFX3 | MEARLLVLLCAFAATNA | SEQ ID NO: 58 |
| P03456 | MEKFIAIATLASTNAY | SEQ ID NO: 59 |
| Q9WCD8 | MKAILLVLLCAFAATNA | SEQ ID NO: 60 |
| Q30NQ1 | MKTIIALSYIFCLAFA | SEQ ID NO: 61 |
| Q2VND2 | MKTIIALSYIFCQVFA | SEQ ID NO: 62 |
| P13101 | MDIQAVALLILTSTCVQA | SEQ ID NO: 63 |
| Q00716 | MKQLSIVILLLSIVYT | SEQ ID NO: 64 |
| Q67282 | MTITFLILLFTVVKG | SEQ ID NO: 65 |
| Q38SQ8 | MKTIIALSYIFCLVFA | SEQ ID NO: 66 |
| P13103 | MALNVIATLTLISVCVHA | SEQ ID NO: 67 |
| P07976 | MERTVIALAIISVVKG | SEQ ID NO: 68 |
| P12440 | MVVTSNA | SEQ ID NO: 69 |
| Q6DQ20 | MKKIVLLLAIVSLVKS | SEQ ID NO: 70 |
| P03442 | MKTVIALSYILCLTFG | SEQ ID NO: 71 |
| Q82509 | MERIVLFLAIVSLVKS | SEQ ID NO: 72 |
| P26135 | MKTIIVLSYFFCLALS | SEQ ID NO: 73 |
| P12439 | MYKVVVIIALLGAVKGL | SEQ ID NO: 74 |
| Q6DQ22 | KIVLLAIVSLVKS | SEQ ID NO: 75 |
| P26094 | MNTQILILATSAFFYVRA | SEQ ID NO: 76 |
| P03447 | MERVVLLLAMISLVKS | SEQ ID NO: 77 |
| P26141 | MKTLIALSYIFCLVLG | SEQ ID NO: 78 |
| P36346 | MNTQILVFALVAVIHTNA | SEQ ID NO: 79 |
| P03448 | MIAIIVVAILATAGRS | SEQ ID NO: 80 |
| P11135 | MEKIVLLFAIVSLVRS | SEQ ID NO: 81 |
| O56140 | MEKTVLLLATVSLVKS | SEQ ID NO: 82 |
| P09345 | MERIVLLLAIVSLVKS | SEQ ID NO: 83 |
| P19694 | MLSVVILFLLVAENSS | SEQ ID NO: 84 |
| P04660 | MKKILLFTVIFLYAKA | SEQ ID NO: 85 |
| P04662 | MEKLLLFATIILCVKA | SEQ ID NO: 86 |
| P19698 | MLSIVVLLLLIAESSS | SEQ ID NO: 87 |
| Q9WCE8 | MEAKLFVLFCAFTTLEA | SEQ ID NO: 88 |
| P03449 | MKTIIALSHIFCLVLG | SEQ ID NO: 89 |
| P19697 | MLSIVVLLLLMAEGSS | SEQ ID NO: 90 |
| P26136 | MIALILVALALSHTAYS | SEQ ID NO: 91 |
| P26140 | MKAILLVLLYTFTAANA | SEQ ID NO: 92 |
| P03452 | MKANLLVLLCALAAADA | SEQ ID NO: 93 |

TABLE 1-continued

Signal Peptides

| Accession Number | Signal Sequence | SEQ ID NO |
|---|---|---|
| P03455 | MKAILLVLLCTFAATNA | SEQ ID NO: 94 |
| P28730 | MKAKLLILFCAFTATDA | SEQ ID NO: 95 |
| Q6J8F6 | MEKIVLLFAIVSLVKS | SEQ ID NO: 96 |
| P03457 | METKAIIAALLMVTAANA | SEQ ID NO: 97 |
| P19700 | MLSITILFLLIAEVSS | SEQ ID NO: 98 |
| P03440 | MKTIIALSYIFCQVLA | SEQ ID NO: 99 |
| P28731 | MKAKLLVLFCAFTATDA | SEQ ID NO: 100 |
| P03461 | VTSNA | SEQ ID NO: 101 |
| P12581 | MYKVVVIIALLGAVRGL | SEQ ID NO: 102 |
| P26137 | LVALALSQTAYS | SEQ ID NO: 103 |
| P12441 | IIVLLMVVTSNA | SEQ ID NO: 104 |
| P03444 | MYKIVLVLTLFGAVNGL | SEQ ID NO: 105 |
| P03458 | MNTQILVFIACVLIKAKG | SEQ ID NO: 106 |
| O11283 | MKTIIALSYILCLVFA | SEQ ID NO: 107 |
| Q9QAQ9 | MFLLPRFVLVSCIIGSLG | SEQ ID NO: 108 |
| P31615 | MCIAMAPRTLLLLIXCQLVF | SEQ ID NO: 109 |
| P15776 | MFLLLRFVLVSCIIGSLG | SEQ ID NO: 110 |
| O91262 | MGSMCIAMAPRTLLLLIGCQLALG | SEQ ID NO: 111 |
| P0C0V9 | MLSLILFFPSFAFA | SEQ ID NO: 112 |
| P30215 | MFLLPRFILVSCIIGSLG | SEQ ID NO: 113 |
| Q14EB1 | MLIIFLFFNFCYG | SEQ ID NO: 114 |
| Q9IKD2 | MGRMCIAMAPRTLLLLIGCQLVFG | SEQ ID NO: 115 |
| Q70KP1 | MLRMRVRPPSAIPVFLIFVLLPFVLTS | SEQ ID NO: 116 |
| Q5MQD1 | MLIIFLFFYFCYG | SEQ ID NO: 117 |
| P31614 | MCIAMAPRTLLLLIGCQLV | SEQ ID NO: 118 |
| O92367 | MARTDAMAPRTLLVLSLGYAFG | SEQ ID NO: 119 |
| Q8JSP9 | MFLLPRFCLVCSIISTFG | SEQ ID NO: 120 |
| Q83356 | MGSTCIAMAPRTLLLLIGCQLV | SEQ ID NO: 121 |
| Q8BB26 | MFLLPRFCLVCSIIGTFG | SEQ ID NO: 122 |
| P68762 | MFFSLLLMLGLTEA | SEQ ID NO: 123 |
| P07975 | MFFSLLLVLGLTEA | SEQ ID NO: 124 |
| P87691 | MLGLTEA | SEQ ID NO: 125 |

Therefore, in some embodiments, the disclosed fusion protein has the amino acid sequence MEAKLFVLFC AFTALKAMGT NLSVPNPLGF FPDHQLDPAF GANS-NNPDWD FNPIKDHWPA ANQVGVGAFG PGLTP-PHGGI LGWSPQAQGI LTTVSTIPPP ASTNRQSGRQ PTPISPPLRD SHPQAMQWNS TAFHQALQDP RVRG-LYLPAG GSSSGTVNPA PNIASHISSI SARTGDPVTN KLESVGVHQI LAIYSTVASS LVLLVSLGAI SFWMCSNGSL QCRICI (SEQ ID NO:2), or a conservative variant thereof having at least about 70%, 75%, 80%, 85%, 90%, 91%, 92%, 93%, 94%, 95%, 96%, 97%, 98%, 98%, 99%, or 100% sequence identity to SEQ ID NO:2 (e.g. 1, 2, 3, 4, 5, 6, 7, 8, 9, or 10 conservative amino acid substitutions).

Also disclosed are polynucleotides comprising nucleic acid sequences encoding the disclosed fusion proteins. For example, the nucleic acid sequences can be operably linked to expression control sequences. Thus, also disclosed are expression vectors for producing the disclosed fusion proteins as well as cells containing these polynucleotides and vectors for replicating the polynucleotides and vectors or to produce the disclose fusion proteins and/or VLPs. Therefore, the disclosed cell can also contain nucleic acid sequences encoding the disclosed fusion protein, including a vector comprising the nucleic acid sequences encoding the disclosed fusion protein.

Also disclosed are polynucleotides comprising nucleic acid sequences encoding the influenza virus M1 protein. For example, the nucleic acid sequences can be operably linked to expression control sequences. Thus, also disclosed are expression vectors for producing the disclosed fusion proteins as well as cells containing these polynucleotides and vectors for replicating the polynucleotides and vectors or to produce the disclose fusion proteins and/or VLPs. Therefore, the disclosed cell can also contain nucleic acid sequences encoding the M1 protein, including a vector comprising the nucleic acid sequences encoding the M1 protein.

Also disclosed is a dual vector comprising a first nucleic acid sequence encoding a disclosed fusion protein and a second nucleic acid sequence encoding an M1 protein. The cell can be a prokaryotic or eukaryotic cell. For example, the cell can be a bacterium, an insect cell, a yeast cell, or a mammalian cell. The cell can be a human cell. Suitable vectors can be routinely selected based on the choice of cell used to produce the VLP. For example, where insect cells are used, suitable vectors include baculoviruses. In case of mammalian cells, plasmids for protein expression may be used.

Fusion proteins, also known as chimeric proteins, are proteins created through the joining of two or more genes which originally coded for separate proteins. Translation of this fusion gene results in a single polypeptide with function properties derived from each of the original proteins. Recombinant fusion proteins can be created artificially by recombinant DNA technology for use in biological research or therapeutics.

The functionality of fusion proteins is made possible by the fact that many protein functional domains are modular. In other words, the linear portion of a polypeptide which corresponds to a given domain, such as a tyrosine kinase domain, may be removed from the rest of the protein without destroying its intrinsic enzymatic capability. Thus, any of the herein disclosed functional domains can be used to design a fusion protein.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

If the two entities are proteins, often linker (or "spacer") peptides are also added which make it more likely that the proteins fold independently and behave as expected. Especially in the case where the linkers enable protein purification, linkers in protein or peptide fusions are sometimes engineered with cleavage sites for proteases or chemical agents which enable the liberation of the two separate proteins.

Virus Like Particles (VLPs)

The disclosed constructs may be expressed on the surface of a particle to mimic the natural conformation of preS on hepatitis B virions. For example, the disclosed fusion proteins may be incorporated into virus-like particles (VLPs) by including within the fusion protein a membrane anchor domain, such as a transmembrane domain and optional cytoplasmic domain of a viral envelope protein.

Non-replicating VLPs resemble infectious virus particles in structure and morphology, and contain immunologically relevant viral structural proteins. VLPs have been produced from both non-enveloped and enveloped viruses. Envelopes of VLPs are derived from the host cells similar to the way as enveloped viruses such as influenza A virus obtain their lipid envelopes from their host cells. Therefore, membrane-anchored proteins on the surfaces of enveloped viruses will be expressed in a native-like conformation if they are expressed in a membrane-anchored form.

Influenza VLPs involve lipid bilayers and host cell membrane proteins (Song, J. M., et al. J Proteome Res 2011 10:3450-3459). For example, Influenza VLPs containing the wild type M2 protein have been described (Song, J. M., et al. Proc Natl Acad Sci USA 2011 108:757-761; Song, J. M., et al. PLoS One 2011 6:e14538). Enveloped VLPs may be composed of influenza matrix 1 (M1) protein as a particle forming core. These VLPs are produced, for example, by coinfecting insect cells with one or more recombinant baculoviruses co-expressing M1 proteins and the disclosed fusion proteins, culturing the insect cells under physiological conditions, and purifying the VLPs from insect cell culture supernatants.

Vaccine Compositions

Disclosed are vaccine compositions that comprise one or more of the fusion proteins described above. Although not required, the vaccine compositions optionally contain one or more immunostimulants. An immunostimulant refers to essentially any substance that enhances or potentiates an immune response (antibody or cell-mediated) to an exogenous antigen. One preferred type of immunostimulant is an adjuvant.

Many adjuvants contain a substance designed to protect the antigen from rapid catabolism, such as aluminum hydroxide or mineral oil, and a stimulator of immune responses, such as lipid A, Bortadella pertussis or *Mycobacterium tuberculosis* derived proteins. The adjuvant may be a submicron oil-in-water emulsion of a metabolizable oil and an emulsifying agent. For example, the adjuvant may comprise MF59™, which is a sub-micron oil-in-water emulsion of a squalene, polyoxyethylene sorbitan monooleate (Tween™ 80) and sorbitan trioleate. The adjuvant may also be a combination of the TLR4 agonist MPL (3-O-desacyl-4'-monophosphoryl lipid A) and aluminum salt, e.g., AS04 (GlaxoSmithKline, Philadelphia, Pa.).

Certain adjuvants are commercially available as, for example, Freund's Incomplete Adjuvant and Complete Adjuvant (Difco Laboratories, Detroit, Mich.); Merck Adjuvant 65 (Merck and Company, Rahway, N.J.); AS01, AS02, AS03, and AS04 (GlaxoSmithKline, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

The adjuvant composition can be a composition that induces an anti-inflammatory immune response (antibody or cell-mediated). Accordingly, high levels of anti-inflammatory cytokines (anti-inflammatory cytokines may include, but are not limited to, interleukin 4 (IL-4), interleukin 5 (IL-5), interleukin 10 (IL-10), and transforming growth factor beta (TGFβ). Optionally, an anti-inflammatory response would be mediated by CD4+ T helper cells. Bacterial flagellin has been shown to have adjuvant activity (McSorley et al., J. Immunol. 169:3914-19, 2002). Also disclosed are polypeptide sequences that encode flagellin proteins that can be used in adjuvant compositions.

Optionally, the adjuvants increase lipopolysaccharide (LPS) responsiveness. Illustrative adjuvants include but are not limited to, monophosphoryl lipid A (MPL), aminoalkyl glucosaminide 4-phosphates (AGPs), including, but not limited to RC-512, RC-522, RC-527, RC-529, RC-544, and RC-560 (Corixa, Hamilton, Mont.).

In addition, the adjuvant composition can be one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a subject will support an immune response that includes Th1- and Th2-type responses. Optionally, the level of Th1-type cytokines will increase to a greater extent than the level of Th2-type cytokines. The levels of these cytokines may be readily assessed using standard assays. Certain adjuvants for eliciting a predominantly Th1-type response include, for example, a combination of monophosphoryl lipid A, preferably 3-de-O-acylated monophosphoryl lipid A, together with an aluminum salt adjuvants are available from Corixa Corporation (Seattle, Wash.). CpG-containing oligonucleotides (in which the CpG dinucleotide is unmethylated) also induce a predominantly Th1 response. Another adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins.

Additional illustrative adjuvants for use in the disclosed vaccine compositions include Montamide ISA 720 (Seppic, France), SAF (Chiron, Calif., United States), ISCOMS (CSL), MF-59 (Chiron), the SBAS series of adjuvants (e.g., SBAS-2 or SBAS-4, available from GlaxoSmithKline, Philadelphia, Pa.), Detox (Enhanzyn™) (Corixa, Hamilton, Mont.), RC-529 (Corixa, Hamilton, Mont.) and other aminoalkyl glucosaminide 4-phosphates (AGPs).

In some embodiments, the adjuvant is incorporated into the VLP in a membrane-anchored form. For example, GM-CSF or a bacterial flagellin protein containing a membrane anchor can be incorporated into the disclosed VLPs.

Pharmaceutical Compositions

The disclosed vaccines can be used therapeutically in combination with a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The materials may be in solution, suspension (for example, incorporated into microparticles, liposomes, or cells). Suitable carriers and their formulations are described in Remington: The Science and Practice of Pharmacy (22nd ed.) eds. Loyd V. Allen, Jr., et al., Pharmaceutical Press, 2012. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of vaccines to humans, including solutions such as sterile water, saline, and buffered solutions at physiological pH. Pharmaceutical compositions may include carriers, thickeners, diluents, buffers, preservatives, surface active agents and the like in addition to the vaccine. Pharmaceutical compositions may also include one or more active ingredients such as antimicrobial agents, antiinflammatory agents, anesthetics, and the like.

The disclosed vaccines are preferably formulated for delivery via intranasal, intramuscular, subcutaneous, transdermal or sublingual administration.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringers, or fixed oils. Intravenous vehicles include fluid and nutrient replenishers, electrolyte replenishers (such as those based on Ringers dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The disclosed vaccine can be used to supplement existing human vaccines to improve cross protection. Therefore, the disclosed vaccine can further include (or be administered in combination with) a whole inactivated virus, split viral vaccine, live attenuated hepatitis B vaccine, or another hepatitis B virus-like particle (VLP) vaccine, as well as DNA vaccines. For example, the disclosed vaccine can be combined with a hepatitis S vaccine.

The disclosed vaccine can further include (or be administered in combination with) one or more of classes of antibiotics, steroids, analgesics, anti-inflammatory agents, anti-histaminic agents, or any combination thereof. Antibiotics include Aminoglycosides, Cephalosporins, Chloramphenicol, Clindamycin, Erythromycins, Fluoroquinolones, Macrolides, Azolides, Metronidazole, Penicillins, Tetracyclines, Trimethoprim-sulfamethoxazole, and Vancomycin. Suitable steroids include andranes, such as testosterone. Narcotic and non-narcotic analgesics include morphine, codeine, heroin, hydromorphone, levorphanol, meperidine, methadone, oxydone, propoxyphene, fentanyl, methadone, naloxone, buprenorphine, butorphanol, nalbuphine, and pentazocine. Anti-inflammatory agents include alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isofluprdone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium. Anti-histaminic agents include ethanolamines (e.g., diphenhydrmine carbinoxamine), Ethylenediamine (e.g., tripelennamine pyrilamine), Alkylamine (e.g., chlorpheniramine, dexchlorpheniramine, brompheniramine, triprolidine), other anti-histamines like astemizole, loratadine, fexofenadine, bropheniramine, clemastine, acetaminophen, pseudoephedrine, triprolidine).

Methods of Vaccinating a Subject

A method of vaccinating a subject for hepatitis B is disclosed that involves administering the disclosed vaccine to a subject in need thereof. The disclosed vaccine may be administered in a number of ways. For example, the disclosed vaccine can be administered intramuscularly, intranasally, or by microneedle in the skin. The compositions may be administered orally, intravenously, subcutaneously, transdermally (e.g., by microneedle), intraperitoneally, ophthalmically, vaginally, rectally, sublingually, or by inhalation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical dosage of the disclosed vaccine used alone might range from about 1 µg/kg to up to 100 mg/kg of body weight or more per vaccination, such as 10 µg/kg to 50 mg/kg, or 50 µg/kg to 10 mg/kg, depending on the factors mentioned above.

T Cell Expansion for Adoptive Cell Transfer

Also disclosed is a method for activating and expanding CD8+ T cells for adoptive cell transfer (ACT). The method generally involves co-culturing CD8+ T cells and dendritic cells with the VLPs disclosed herein.

ACT may be performed by (i) obtaining autologous lymphocytes from a mammal, (ii) culturing the autologous lymphocytes to produce expanded lymphocytes, and (ii) administering the expanded lymphocytes to the mammal. Preferably, the lymphocytes are isolated from the mammal to be treated, i.e. autologous transfer.

Expanded lymphocytes produced by the disclosed methods can be administered as an intra-arterial or intravenous infusion, which preferably lasts about 30 to about 60 minutes. Other examples of routes of administration include intraperitoneal, intrathecal and intralymphatic. Likewise, any suitable dose of lymphocytes can be administered. In one embodiment, about $1\times10^{10}$ lymphocytes to about $15\times10^{10}$ lymphocytes are administered.

A number of embodiments of the invention have been described. Nevertheless, it will be understood that various modifications may be made without departing from the spirit and scope of the invention. Accordingly, other embodiments are within the scope of the following claims.

EXAMPLES

Example 1: A Virus-Like Particle Vaccine of the Hepatitis B Virus preS Antigen Protects Mice Against Challenge There are three envelope proteins in the HBV virion, S, M and L. The preS protein is part of the L protein, a 163 amino acid extension at the N-terminus of the S protein (genotype A). preS may be further divided as preS1 (a.a.1-108) and preS2 (a.a.109-163). In the M protein, only preS2 is present at the N-terminus in addition to the amino acids that are common among the S, M and L proteins (Churin Y, et al. Hepatobiliary Surg Nutr 2015 4:1-10). Two well-known functions are related to preS. First of all, preS includes the region that interacts with the specific host receptor (Yan H, et al. Elife 2012 1:e00049). Further studies define the interaction motif to be within the first 48 amino acids of preS (Barrera A, et al. J Virol 2005 79:9786-9798; Glebe D, et al. Gastroenterology 2005 129:234-245; Gripon P, et al. J Virol 2005 79:1613-1622). The other important function of preS is that in the preS region, there are highly immunogenic sites as B and T cell epitopes (Vento S, et al. Immunology 1987 62:593-598). It has been reported that preS could induce humoral responses in mice which were nonresponsive to the S antigen, indicating that preS represents a potential antigen for novel HBV vaccine candidates (Milich D R. Immunol Today 1988 9:380-386). Notably, humoral response may play a major role in preventing HBV spread to uninfected cells. Besides, it is generally believed that a proper CD4+ helper T cell response is a prerequisite for an adequate humoral response (Celis E, et al. J Immunol 1984 132:1511-1516). Furthermore, T cell responses may help extend the longevity of humoral immunity (Bauer T, et al. Vaccine 2006 24:572-577; Wiegand J, et al. J Viral Hepat 2010 17:631-639). However, how these preS epitopes are related to virus clearance is not very clear. It is widely accepted that the CD8$^+$ T cell response is primarily responsible for HBV clearance in both cytopathic and noncytopathic manner (Chisari F V, et al. Pathol Biol 2010 58:258-266). More recent studies demonstrate that HBV-specific CD8$^+$ T cells are able to clear HBV-infected hepatocytes by secretion of antiviral cytokines, such as IFN-γ, and TNF-α (Kosinska A D, et al. Hepat Res Treat 2010 2010:817580).

Virus-like particles (VLPs) resemble authentic native viruses in structure and morphology, but are non-infectious, because they assemble without containing genetic material. Compared to individual proteins or peptides, VLPs significantly improve humoral responses by presenting conformational epitopes more similar to the native virus. Owing to their highly repetitive surface, VLPs are capable of eliciting robust B cell responses in the absence of adjuvants by efficiently cross-linking specific receptors on B cells (Roldao A, et al. Expert Rev Vaccines 2010 9:1149-1176). Besides, VLPs could also induce potent cytotoxic T lymphocyte (CTL) responses in immunized animals (Liu X S, et al. Virology 1998 252:39-45).

A virus-like particle (preS VLP) that contains the matrix protein M1 from influenza virus and the transmembrane domain and cytoplasmic tail of influenza virus hemagglutinin (HA) to form the scaffold was produced. The HBV preS antigen was presented on the surface of VLP by fusing it with the HA fragment. The immunogenicity of preS VLP was assessed as a potential vaccine candidate. Immunization with preS VLP induced both potent humoral and cellular immune responses, and protected mice from HBV challenge.

Materials and Methods

Plasmids and Cells

The vector for expressing HBV preS (adw subtype, Accession Number AGW20902) in E. coli (pET28b-preS) was constructed previously (Lian M, et al. Virol J 2007 4:93). The His-tagged preS protein was expressed and purified as described previously (Lian M, et al. Virol J 2007 4:93). The plasmids for expressing M1 protein (the matrix protein) of influenza virus A/sw/Spain/53207/04 and a preS-HA (HA=hemagglutinin) chimeric protein were constructed by inserting the coding sequence in pCAGGS. The amino acid 41 of M1 was mutated to Ala (pCAGGS-M1). The preS-HA has the sequence of HBV preS followed by aa521-566 of HA (pCAGGS-preS-HA). 293T cells were maintained in DMEM supplemented with 10% fetal bovine serum (FBS).

Indirect Immunofluorescence 293T cells were grown on glass coverslips and transfected with pCAGGS-M1 and pCAGGS-preS-HA. 48 hr posttransfection, cells were fixed with 4% paraformaldehyde. Cells were classified into two groups. One was permeabilized with 0.2% Triton X-100 for 5 min, the other without permeabilization. After blocking for 1 h in PBS containing 5% goat serum, all cells were incubated with polyclonal rabbit anti-preS sera at 4° C. overnight. Cells were washed with PBS following incubation with Alexa Fluor® 488-Conjugated goat anti-rabbit secondary antibody for 1 h at 37° C. After washing, cells were stained with DAPI for 10 min, and then mounted onto microscope slides. Confocal slices were acquired with a 100× objective, using a Zeiss 510 confocal microscope with random sampling.

Preparation and Characterization of the Virus-Like Particles

The pCAGGS-M1 and pCAGGS-preS-HA plasmids were transfected into 293T cells with polyethylenimine. 72 hr after transfection, the culture medium was centrifuged at 6000 rpm for 15 min at 4° C. to remove cellular debris, followed by centrifugation at 22,000 rpm for 3 hr at 4° C. The pellet was resuspended in PBS at 4° C. overnight, and further purified through a 20%-60% sucrose gradient in a Beckman SW41Ti rotor at 30,000 rpm for 3 hr at 4° C. The 40% sucrose fraction was harvested and diluted with PBS by about 5 fold. After centrifugation at 22,000 rpm for 3 hr at 4° C. to remove the sucrose, the virus-like particles were resuspended in PBS at 4° C. overnight. A sample was applied to a 400 mesh carbon-coated copper grid, and stained with 1% phosphotungstic acid (J&K Scientific). preS VLP was visualized on a Tecnai G² Spirit transmission election microscope operating at 120 kV.

LC-MS/MS Analysis

The expression of M1 and preS-HA was analysed by LC-MS/MS. Briefly, 40% sucrose fraction were subjected to electrophoresis on a 12%-SDS-PAGE gel, which was stained by coomassie R250. The coomassie R250 stained gel bands were cut, followed by in-gel digestion with trypsin [Promega, enzyme:protein=1:50 (wt/wt)] at 37° C. for 12 h in 25 mM ammonium bicarbonate buffer. The lyophilized tryptic digested samples were re-dissolved in 2% acetonitrile, 0.1% formic acid, and loaded on ChromXP C18 (3 µm, 120 Å) nanoLC trap column. The online trapping, desalting procedure was carried out at a flow rate of 2 µL/min for 10 min with 100% solvent A (Solvent A: water/acetonitrile/formic acid=98/2/0.1% solvent B: 2/98/0.1%). Then, an 60-min gradient elution ranging from 5-35% acetonitrile (0.1% formic acid) was used on an analytical column (75 µm×15 cm C18-3 µm 120 Å, ChromXP Eksigent). LC-MS/MS analysis was performed with a Triple TOF 5600 System (AB SCIEX, Concord, ON) fitted with a Nanospray III source (AB SCIEX, Concord, ON). Data was acquired using an ion spray voltage of 2.5 kV, curtain gas of 30 PSI, nebulizer gas of 5 PSI, and an interface heater temperature of 150° C. The MS was operated with TOF-MS scans. For IDA, survey scans were acquired in 250 ms and as many as 25 product ion scans (90 ms) were collected if exceeding a threshold of 150 counts per second (counts/s) and with a +2 to +4 charge-state. A Rolling collision energy setting was applied to all precursor ions for collision-induced dissociation. Dynamic exclusion was set for ½ of peak width (~12 s). For data analysis, the .wiff files were processed by ProteinPilot 5.0. Searches were performed against the local database including the protein sequences for M1 and preS-HA, using the default settings.

Immunization and Challenge

Female Balb/c mice of 6-8 weeks old were immunized by injecting the antigen preparation in the hindlimb. A booster was given on day 22. Blood was collected on day 52, and 112, and neutralizing antibody titers were determined by ELISA. On day 52, activated T cells in splenocytes or intrahepatic leukocytes were analysed by ELISPOT and FACS. The immunized mice were challenged on day 70. 10 µg of pT-HBV1.3 (a plasmid containing 1.3 genome length of HBV) was injected under hydrodynamic conditions to establish HBV infection as previously described (Yang P L, et al. Proc Natl Acad Sci USA 2002 99:13825-13830). Hydrodynamic injection of viral DNA is an accepted mouse model of acute hepatitis B virus infection. Blood samples were collected at different time points to measure HBV antigens. On day 67, mice were sacrificed and liver tissues were used for measuring antigens and RNA of HBV. Activated T cells were also analysed by FACS and ELISPOT assay. All mouse experiments were conducted in accordance with the institutional guidelines following the experimental protocol reviewed and approved by the Committee for Animal Experiments at Peking University.

Immunization in HBV Transgenic Mice

All mouse experiments were performed in accordance with the institutional guidelines following the experimental protocol reviewed and approved by the Institutional Animal Care and Use Committee of Peking University. Six- to 8-week-old female HBV transgenic mice (ayw subtype) were obtained from Infectious Disease Center of No. 458 Hospital (Guangzhou, China). HBV transgenic mice were immunized intramuscularly with 20 µg of preS VLP in the hindlimb, and were boosted on days 22 and 43, respectively. Blood was collected on days 0, 30 and 70, and anti-preS antibody titers were determined by ELISA. On day 70, activated T cells in splenocytes were analyzed by ELISPOT and flow cytometry. All mouse experiments were conducted in accordance with the institutional guidelines following the experimental protocol reviewed and approved by the Committee for Animal Experiments at Peking University.

Isolation of Splenocytes and Intrahepatic Leukocytes

For the isolation of splenocytes, splenocytes were gently grinded followed by passaging through 40 μm strainers and treating with ACK lysing buffer. After washing with PBS, cells were resuspended in DMEM supplemented with 10% fetal bovine serum (FBS) and 1% Penicillin-Streptomycin-L-Glutamine. For the isolation of intrahepatic leukocytes, mice livers were perfused with pre-warmed Hanks' balanced solution without $Ca^{2+}$, $Mg^{2+}$, followed by perfusing with 20 mL 0.025% collagenase D in Hanks' balanced salt solution, and let sit for 10 min at 37° C. Livers were then gently grinded followed by passaging through 40 μm strainers. After centrifugation, cells were resuspended in 40% (vol/vol) Percoll in DMEM, and layered over 70% Percoll in PBS (vol/vol). After centrifugation of the gradient for 20 min at 2000 rpm, the cells at the interphase were collected. The cells were then treated with ACK lysing buffer, washed with PBS, and resuspended in DMEM supplemented with 10% fetal bovine serum (FBS) and 1% Penicillin-Streptomycin-L-Glutamine for further analysis.

Enzyme-Linked Immunospot Assay

T cell responses were determined using an IFN-γ ELISPOT set (BD Biosciences) following the manufacturer's protocol. Briefly, 96-well plates were coated with purified anti-mouse IFN-γ antibody (1:200) at 4° C. overnight, and then were blocked for 2 h using DMEM supplemented with 10% fetal bovine serum (FBS) and 1% Penicillin-Streptomycin-L-Glutamine. Splenocytes or intrahepatic leukocytes were seeded at $2 \times 10^5$/well. Peptides representing previously described epitopes present in preS (Table 1) or purified preS protein were used to stimulate cells for 36 h at 37° C. in a 5% $CO_2$ and humidified incubator, with media and phorbol myristate acetate (PMA)/ionomycin-treated cells used as negative and positive controls, respectively. After being washed, cells were incubated with biotinylated anti-mouse IFN-γ antibody (1:250) for 2 h at room temperature, and then incubated with streptavidin-horseradish peroxidase (HRP) (1:1,000) for 1 h. Following the final washes, 3-amino-9-ethylcarbazole (AEC) substrate (Alfa Aesar) was added to the wells and allowed to develop at room temperature for 40 min. The reaction was stopped with distilled water, and the plates were allowed to air dry before spot-forming cells were enumerated by using an ELISPOT plate reader.

TABLE 2 preS-specific T cell epitopes.

| Epitope | Residues | Amino acid sequence | Reference |
|---|---|---|---|
| 1 | preS1 10-19 | PLGFFPDHQL (SEQ ID NO: 12) | * |
| 2 | preS1 41-56 | WPAANQVGVGAFGPGL (SEQ ID NO: 13) | ** |
| 3 | preS2 109-134 | MQWNSTAFHQALQDPRVRGLYLPAGG (SEQ ID NO: 14) | *** |

* Ferrari C, et al. Gastroenterology 1992 103:255-263.
** Doh H, et al. FEMS Immunol Med Microbiol 2003 35:77-85.
*** Pajot A, et al. Microbes Infect 2006 8:2783-2790

Flow Cytometry

Splenocytes or intrahepatic leukocytes were resuspended in DMEM supplemented with 10% fetal bovine serum and 1% Penicillin-Streptomycin-L-Glutamine, and then were seeded at $2 \times 10^6$/well. The cells were then stimulated for 6 h with preS-specific peptides or purified recombinant preS diluted to a final concentration of 10 μg/ml in DMEM supplemented with 2 μg/ml brefeldin A (BD Biosciences). The cells were then washed in staining buffer (PBS containing 2% fetal bovine serum) and stained for CD8 and CD4 surface expression for 30 min at 4° C. using fluorescein isothiocyanate (FITC)-conjugated anti-mouse CD8 antibody (BD Biosciences) and peridinin chlorophyll protein(PerCP)-conjugated anti-mouse CD4 antibody (BD Biosciences). Then the cells were washed, fixed, and permeabilized using a commercially available Cytofix/Cytoperm kit (BD Biosciences). The cells were then stained for 40 min at 4° C. for intracellular cytokine expression using phycoerythrin (PE)-conjugated anti-mouse IFN-γ antibody (BD Biosciences). After washing, cells were resuspended in staining buffer and analysed using a BD FACS Canto™ II flow cytometer (BD Biosciences) and FACSDiva Version 6.1.3. Results were generated from data gathered from 200,000 cells.

ELISA

Purified preS antigen (5 μg/ml) or preS VLP (1 μg/ml) was absorbed to 96 well plates, blocked with 10% BSA, and then 50 μl of 1:100 dilution of sera was incubated for 30 min at 37° C. followed by incubation with added HRP-conjugated anti-mouse IgG, IgG1 or IgG2a (Santa Cruz Biotechnology) for 30 min at 37° C., and then with TMB substrate for 10 minutes before stopping with 2 M $H_2SO_4$ for measurement of optical density at 450 nm. In addition, serum samples were diluted 1:5 for HBsAg ang HBeAg detection.

Neutralization

For infection experiments, $5 \times 10^5$ HepG2/hNTCP cells per well were cultured in 24-well plate and incubated overnight with the viral inoculum (M.O.I. of 500) alone or together with various dilutions of mouse anti-preS VLP sera or 1,000 fold dilution of hepatitis B immunoglobulin (HBIG) (from Chengdu Rongsheng Bioproduct Company, with a protein concentration of 144 mg/ml), with 4% PEG present during virus infection. Medium was changed every 2 or 3 days, and HBeAg was measured at 1 week post infection using Diagnostic ELISA Kit for Hepatitis B e antigen (Kehua Bioengineering).

qPCR Analysis

For detecting mRNA in 293T cells transfected with expression vectors, 48 hr posttransfection, total RNAs from 293T cells were extracted using the QIAGEN RNeasy Mini Kit following the manufacturer's instructions. Total RNAs were stored at −20° C. until being used. Any possible contaminating DNA was erased by DNase I (Takara). Total RNAs were quantified using the NanoDrop 2000 spectrophotometer (Thermo Scientific). 1 μg total RNAs were reverse transcribed into cDNA using the PrimeScript RT Reagent Kit with gDNA Eraser (Takara) in a 20 μL reaction as previously described (Zheng W, et al. Cell Chem Biol 2016 23:1002-1013). cDNA derived from 5 ng total RNAs was used as template for real-time PCR amplification. Primers (preS-HA-FW: 5'-CCACCAATCGGCAGTC-3' (SEQ ID NO:4)) and (preS-HA-RV: 5'-GCCACCAGCAG-GAAGAT-3' (SEQ ID NO:5)) were used for preS-HA transcripts; (M1-FW: 5'-TGACAACAACCAACCCACT-3' (SEQ ID NO:6)) and (M1-RV: 5'-CTGCTGCTTGCT-CACTCG-3' (SEQ ID NO:7)) were for M1 transcripts; (β-actin-FW: 5'-TCATGAAGTGTGACGTGGACATC-3' (SEQ ID NO:8)) and (β-actin-RV: 5'-CAGGAGGAGCAAT-GATCTTGATCT-3' (SEQ ID NO:9)) were used for β-actin transcripts. qRT-PCR was performed with GoTaq qPCR Master Mix (Promega) following the manufacturer's protocol for a total reaction volume of 20 μL in the CFX96 Real-Time PCR Detection System (Bio-Rad). The reaction product was subjected to agarose gel electrophoresis.

For challenge studies, total RNAs from the liver of HBV-challenged mice were isolated with Trizol reagent (Invitrogen). Then chloroform was added and mixed. After centrifugation, the aqueous layer was carefully collected and mixed with isopropanol and let sit for 10 min. After centrifugation, the supernatant was aspirated, and the precipitation was washed with 70% ethanol, followed by dissolved with nuclease-free water. Any possible contaminating DNA was erased by DNase I (Takara). Total RNAs were quantified using the NanoDrop 2000 spectrophotometer (Thermo Scientific). 1 μg total RNAs were reverse transcribed into cDNA using the PrimeScript RT Reagent Kit with gDNA Eraser (Takara) in a 20 μL reaction as previously described (Zheng W, et al. Cell Chem Biol 2016 23:1002-1013). cDNA derived from 2 ng total RNAs was used as template for real-time PCR amplification. Primers (HBV2270FW: 5'-GAGTGTGGATTCGCACTCC-3' (SEQ ID NO:10)) and (HBV2392RV: 5'-GAGGCGAGGGAGTTCTTCT-3' (SEQ ID NO:11)) were used for HBV RNA transcripts (Yan H, et al. Elife 2012 1:e00049). qRT-PCR was conducted with GoTaq qPCR Master Mix (Promega) following the manufacturer's instructions for a total reaction volume of 20 μL in the CFX96 Real-Time PCR Detection System (Bio-Rad).

Immunohistochemistry

Liver tissue was collected and fixed in 10% neutral formalin. After paraffin embedding, liver sections were used to detect HBV core antigen by immunohistochemical staining using polyclonal rabbit anti-HBcAg antibody (Dako).

Results

Construction and Preparation of preS VLP

Figure 1B:
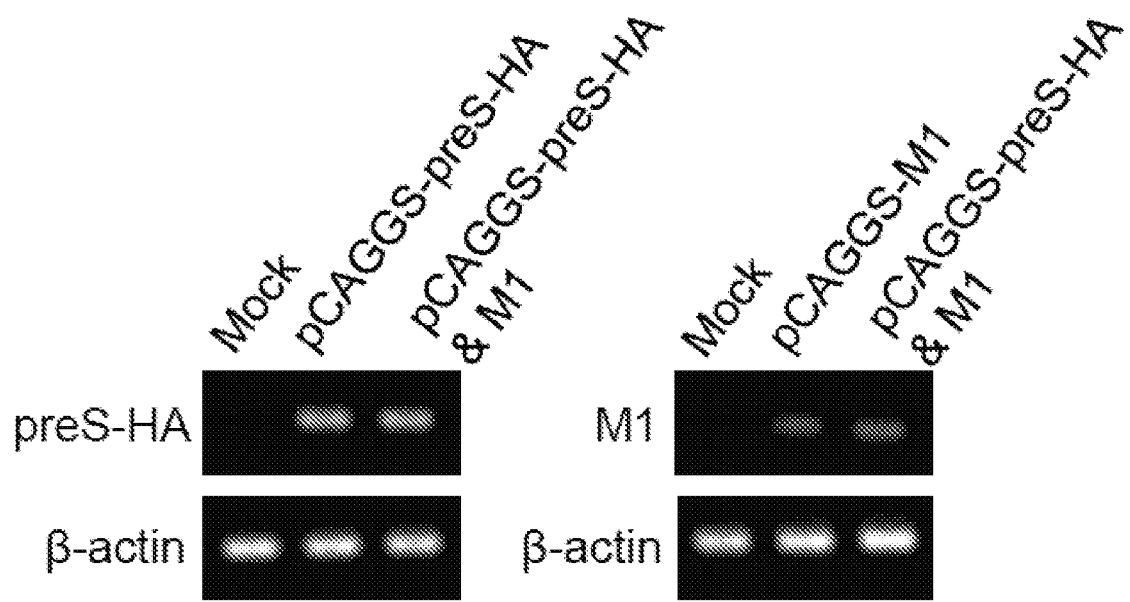
Figure 1C:
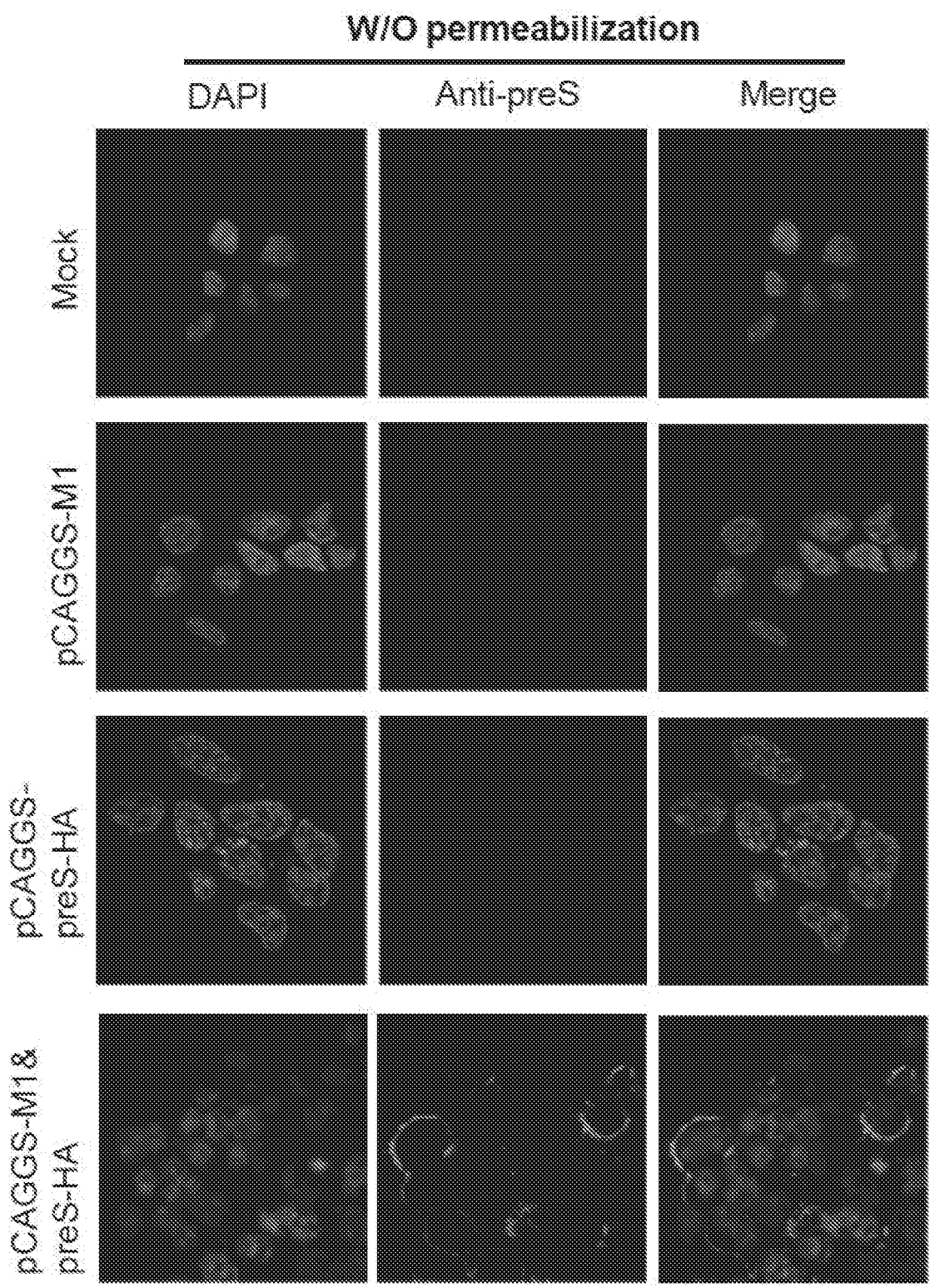
Figure 1D:
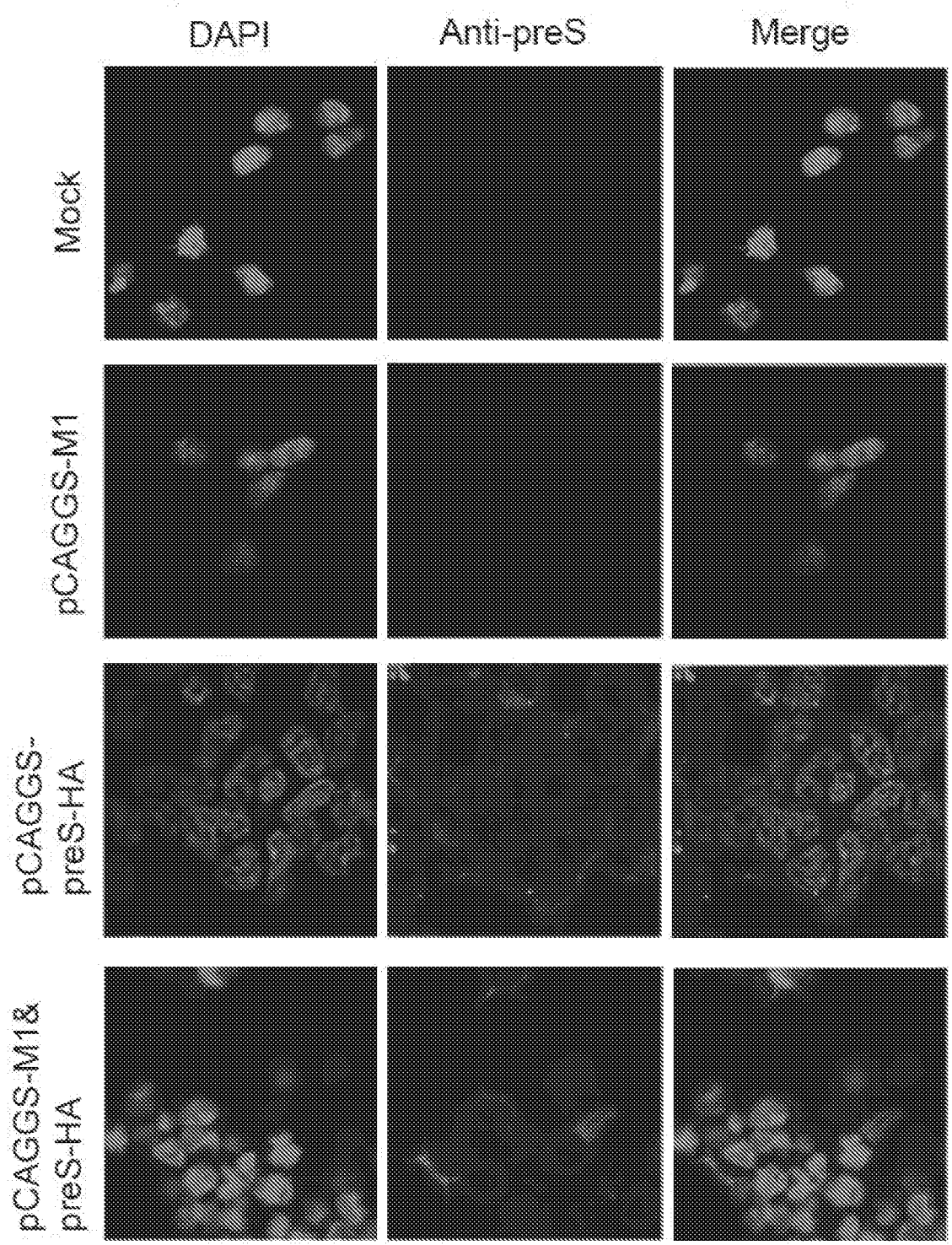

Co-expression of influenza virus M1 and HA releases a virus-like particle decorated with HA antigen (Galarza J M, et al. Viral Immunol 2005 18:244-251). In order to generate a virus-like particle that is decorated with HBV preS antigen, a chimeric protein was constructed that has the preS sequence fused at the N-terminus of a HA fragment that includes its transmembrane domain and the cytoplasmic tail (FIG. 1A). The signal peptide from HA was also added in front of the preS sequence which may be removed after the chimeric protein is expressed. The amino acid 41 of M1 was mutated to Ala to enhance the release of the virus-like particle (Campbell P J, et al. J Virol 2014 88:7569-7577). After transfection of 293T cells with pCAGGS-M1, pCAGGS-preS-HA, or both plasmids, respectively, total RNAs were extracted by QIAGEN RNeasy Mini Kit and analysed for the transcription levels of M1 and preS-HA. The qPCR results suggested that both M1 and preS-HA genes had been transcribed adequately in 293T cells 48 hr after transfection (FIG. 1B). After co-transfection of pCAGGS vectors expressing M1 and preS-HA, respectively, into 293T cells, expression of the preS antigen was readily detected on the cellular membrane by immunofluorescent microscopy (FIGS. 1C and 1D). This is consistent with the construction of the preS-HA chimeric protein because the transmembrane domain of HA retains the chimeric protein in the cellular membrane. If the M1 protein was not co-expressed, the preS-HA chimeric protein appeared to be unable to expose the preS antigen on the exterior of the cellular membrane because the preS antigen was only detectable after the cellular membrane was permeabilized with Triton X-100. Western blot analysis also confirmed the expression of preS-HA in 293T cells (FIG. 2). Interestingly, the presence of preS-HA was detected in the supernatant only when the M1 protein was co-expressed, suggesting that M1 is required for the secretion of preS-HA from cells (FIG. 2A).

Purification and Characterization of preS VLP

Figures 2D, 2E:
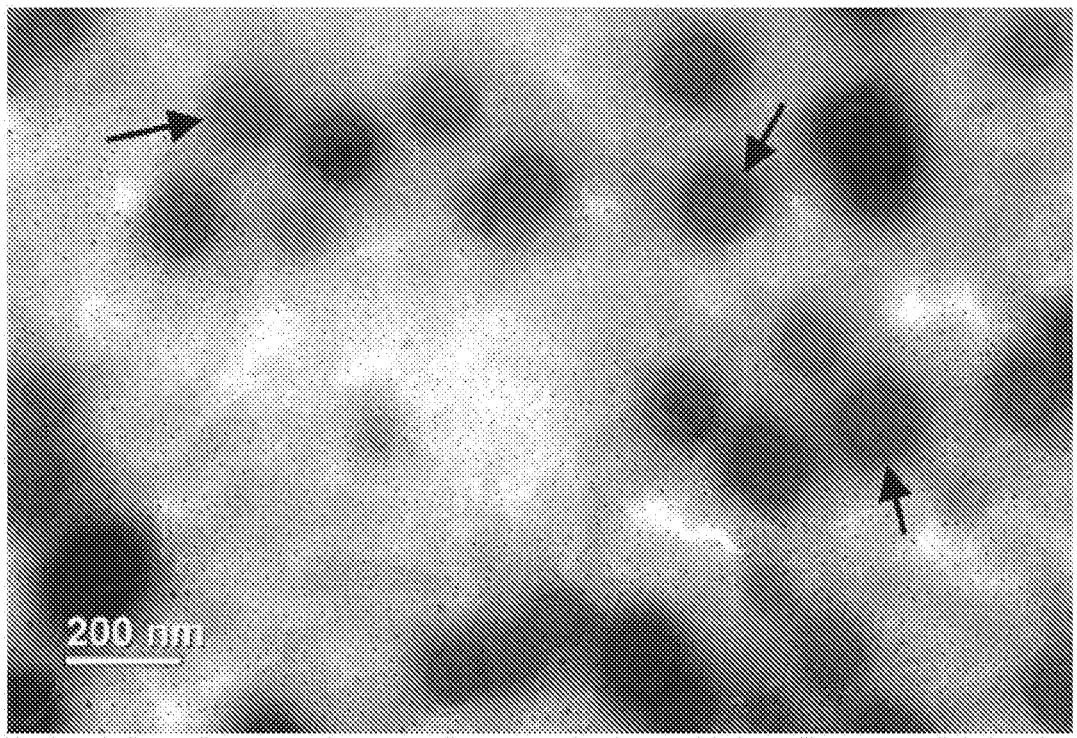

The culture media were collected from the cells that were cotransfected with pCAGGS-M1 and pCAGGS-preS-HA at 72 hr after transfection. The culture media were laid on a sucrose gradient and subjected to ultracentrifugation. A sample was collected from the 40% sucrose fraction. By SDS-PAGE and western blot analysis, the protein corresponding to the preS-HA antigen was identified (FIGS. 2B and 2C). A negative stain electron micrograph showed that this sample contains virus-like particles (FIG. 2D). The sample was further characterized by LC-MS/MS (FIG. 2E). The M1 sequence identified by MS analysis covered above 90% of the full length M1 sequence. However, only two peptides with high confidence (95%) in preS-HA were identified, which may be resulted from the glycosylation of preS (Lambert C, et al. Virol J 2007 4:45). These data showed that VLPs composed of M1 and preS-HA proteins were successfully purified.

Immunization with preS VLP

Balb/c mice were immunized each with 10 μg of the preS antigen as VLP, or recombinant preS purified from *E. coli* expression (Lian M, et al. Virol J 2007 4:93) with alum adjuvant, respectively. PBS was also used as a blank control. A booster was given on day 22. A blood sample was collected from each mouse on day 52 and 112, and sera were prepared from these samples. All sera samples were diluted by 100 fold and the serum antibody titers were determined by ELISA as shown in FIG. 3. The data revealed that VLP is a more potent preS antigen than recombinant preS protein in generating anti-preS neutralizing antibodies, even without the use of any adjuvant. In particular, preS VLP elicited high level total IgG including both anti-preS IgG1 (Th2 isotype) and IgG2a (Th1 isotype).

Figure 3A:
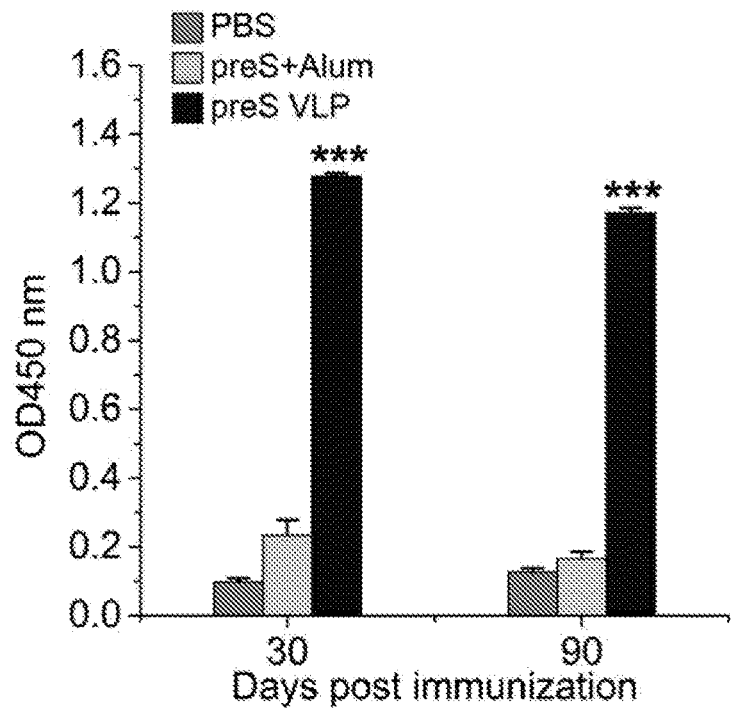
FIGS. 3A to 3D show preS VLP elicits superior HBV-specific humoral immune responses compared to recombinant preS vaccination.
Figure 3B:
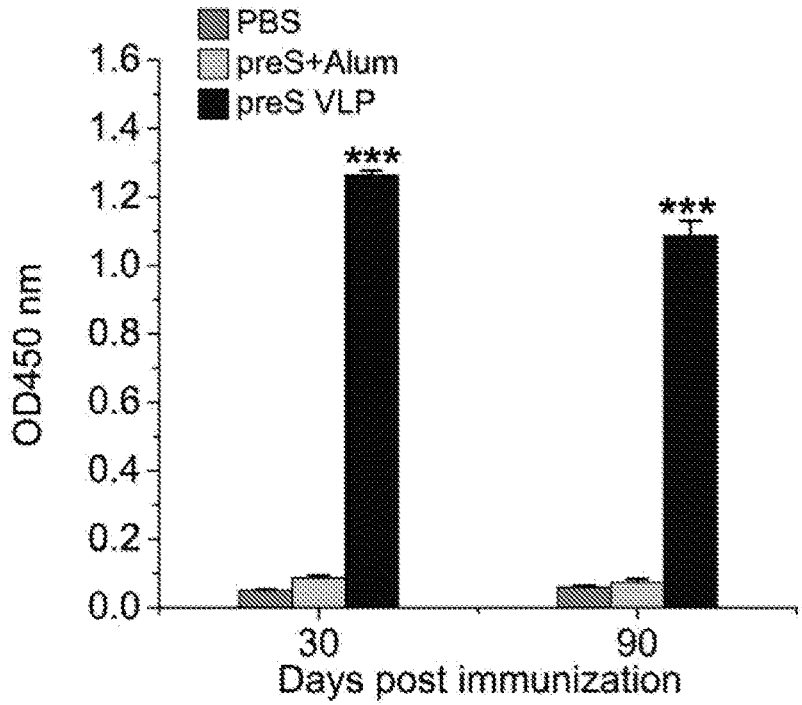
Figure 3C:
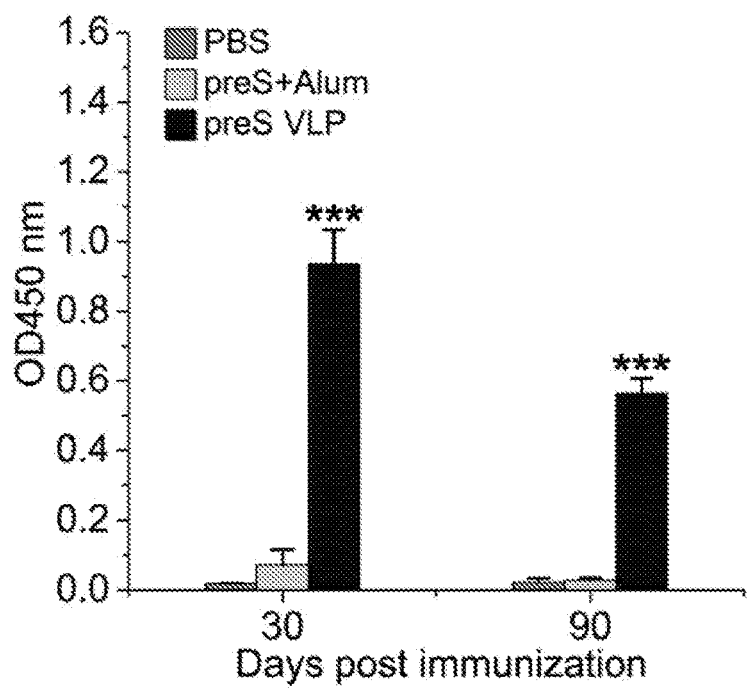
Figure 3D:
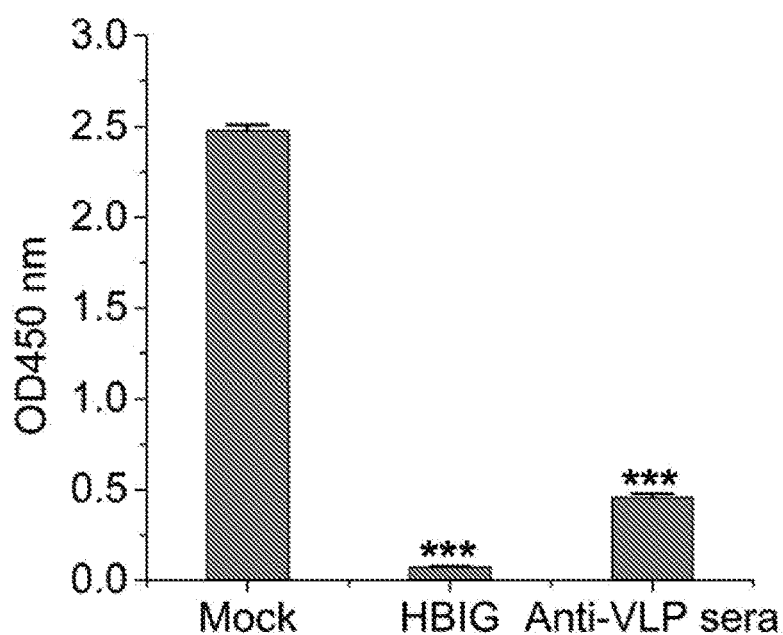

To further test whether anti-preS VLP sera could block HBV infection of human hepatocytes, in vitro infection experiments were conducted. Using hepatitis B immunoglobulin (HBIG) as a positive control, the anti-preS VLP sera clearly prevented HBV from infecting HepG2/hNTCP cells, as demonstrated by a decreased level of HBeAg in the supernatant of cell culture (FIG. 3E). Collectively, these results indicate that preS VLP can stimulate anti-preS neutralizing antibodies in mice.

Figure 4A:
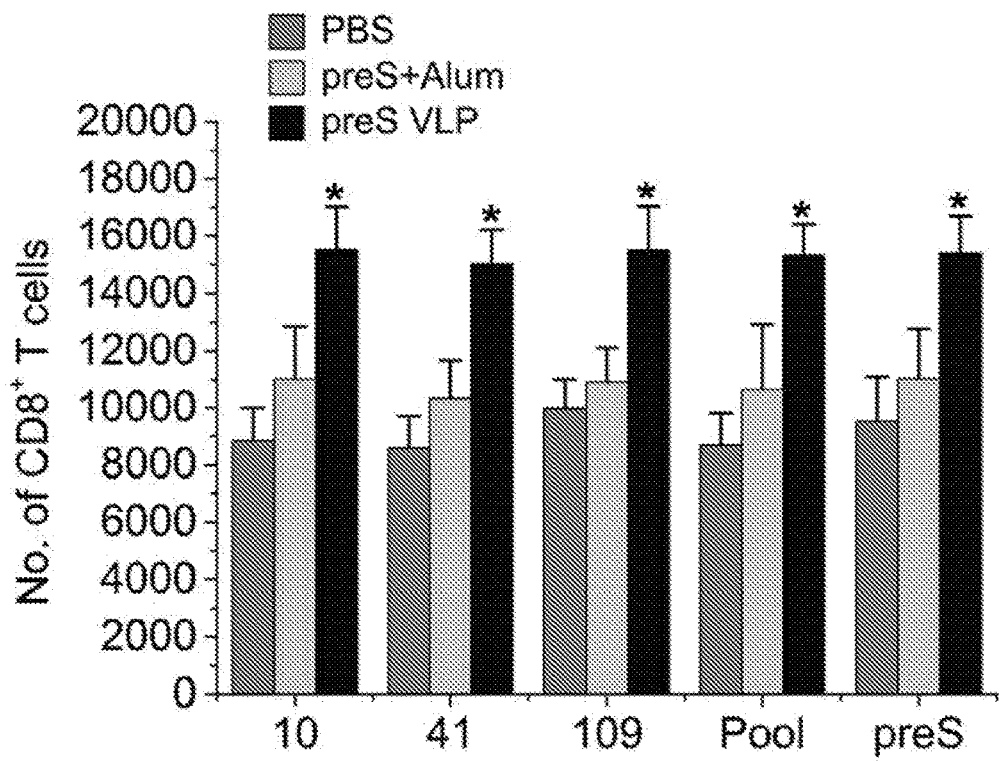
FIGS. 4A to 4E show preS VLP induces stronger T cell responses than recombinant preS vaccination. Balb/c mice were immunized intramuscularly with preS VLP (n=6), recombinant preS protein (n=6), or PBS (n=6). 30 days post immunization, splenocytes were isolated and analyzed for CD8 (FIG. 4A, 4C), CD4 (FIG. 4B, 4D), and IFN-γ (FIG. 4C, 4D) expression by flow cytometry (FIGS. 4A-4D) or ELISPOT assays (FIG. 4E).
Figure 4B:
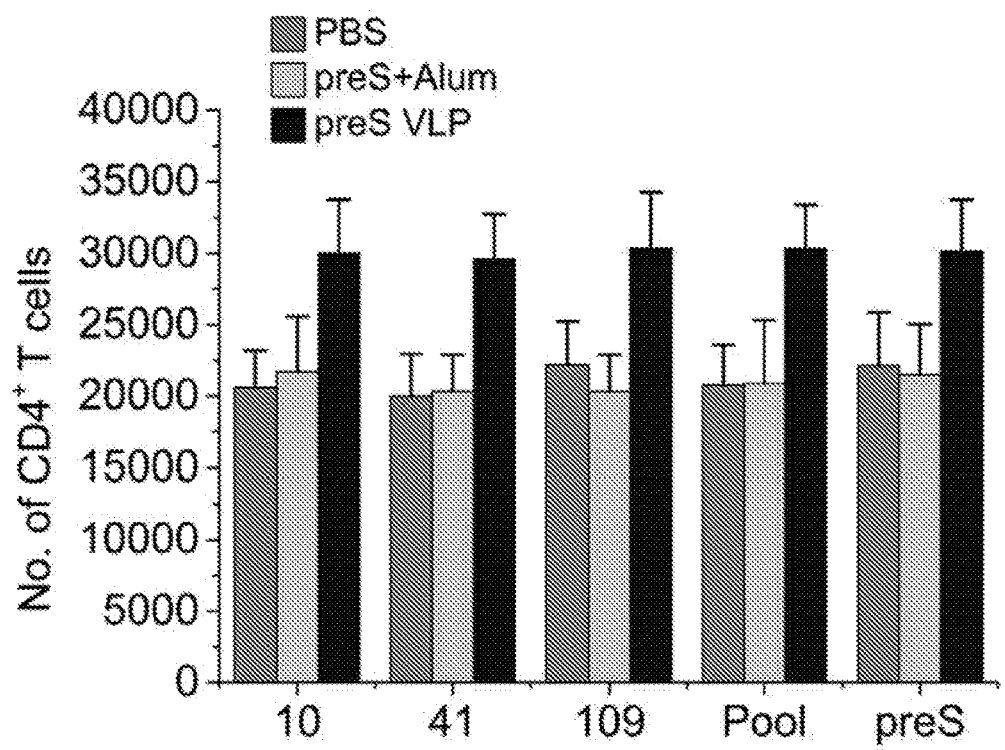
Figure 4C:
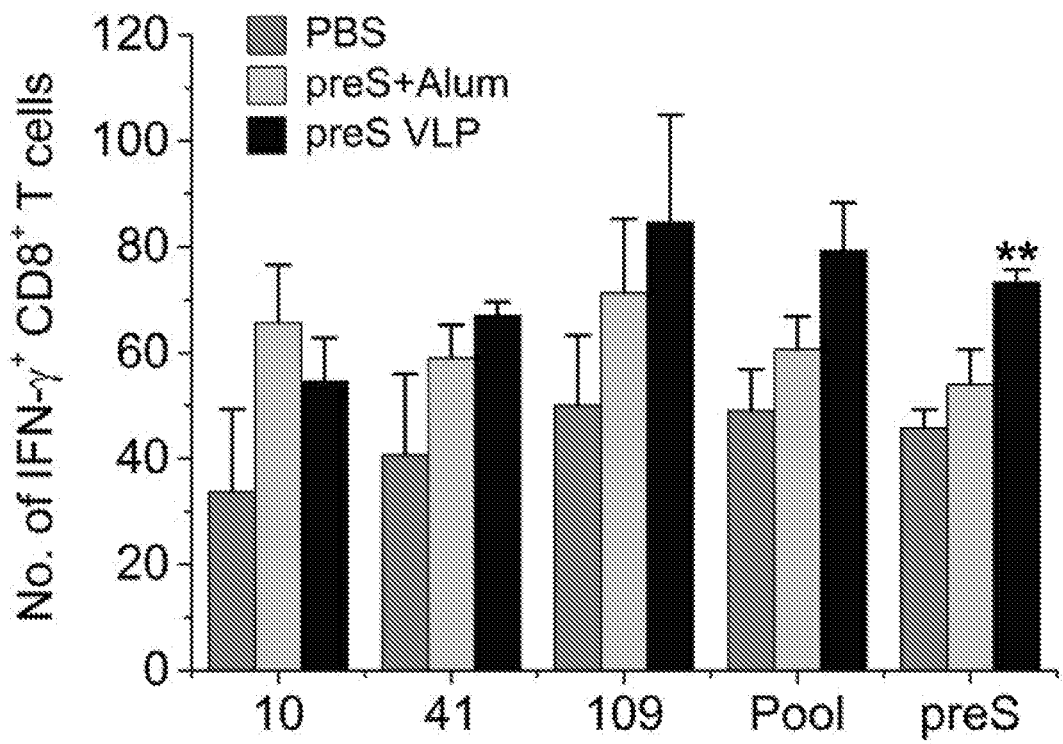
Figure 4D:
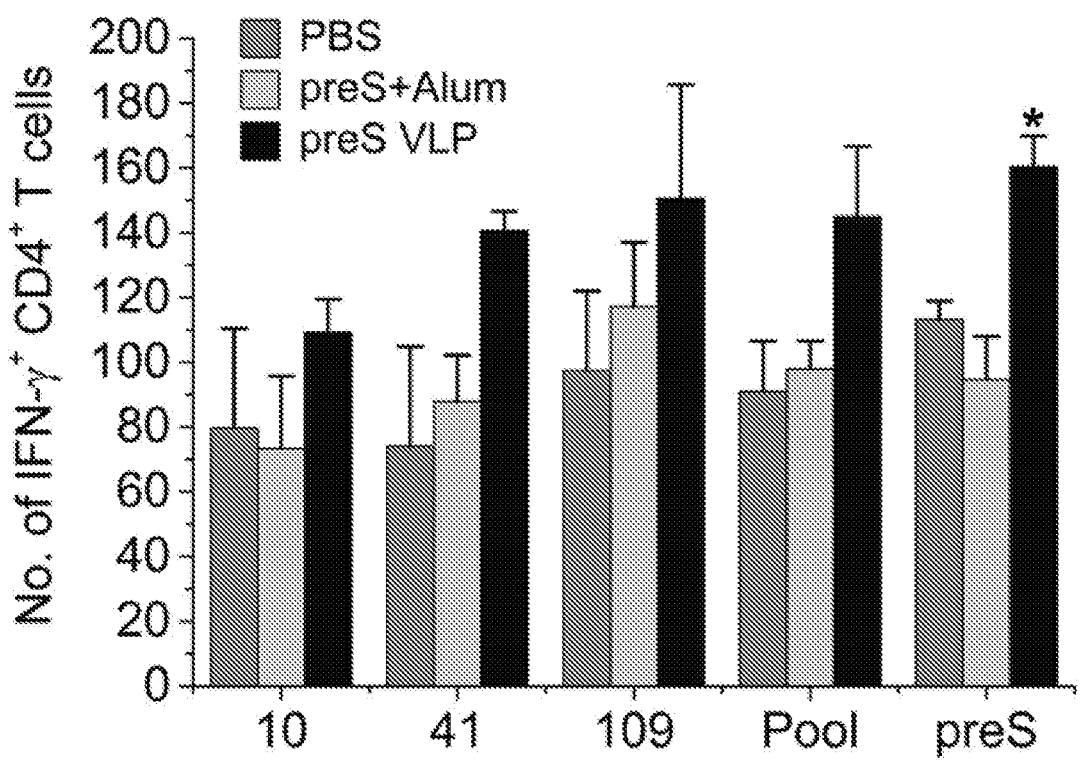
Figure 4E:
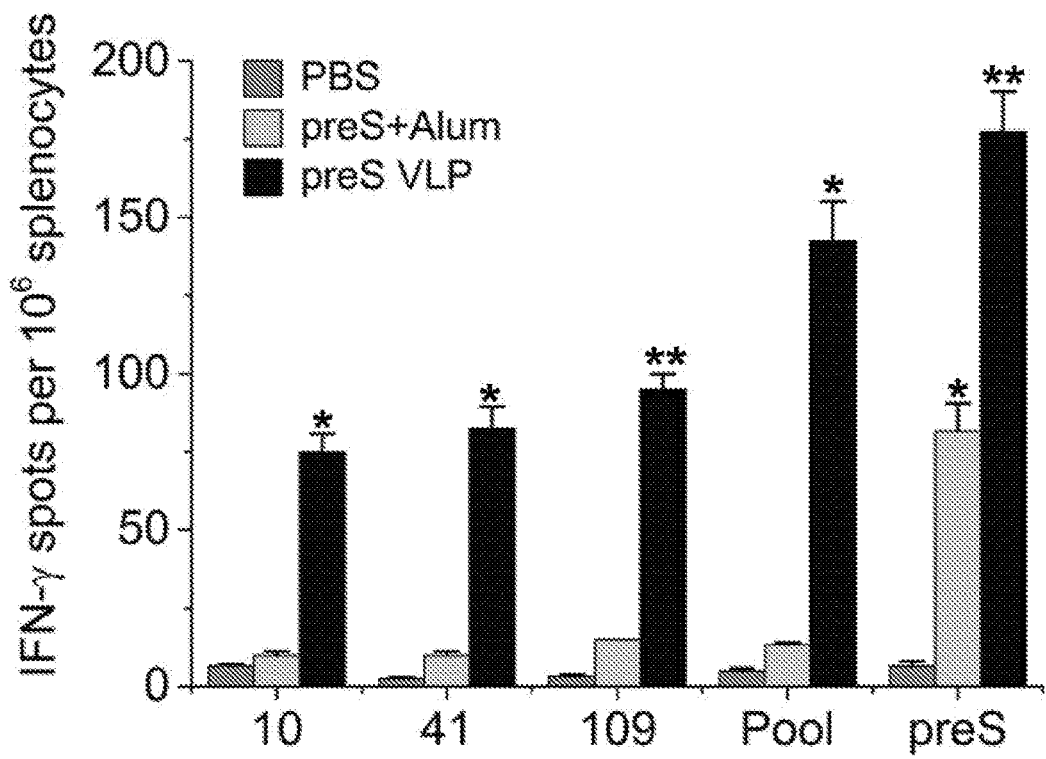

T cell responses play a role in the induction of humoral immunity, and are crucial to effectiveness of a therapeutic HBV vaccine (Celis E, et al. J Immunol 1984 132:1511-1516; Chisari F V, et al. Pathol Biol 2010 58:258-266). To evaluate if preS-specific T cell responses were produced, T lymphocytes from spleen were isolated and cultured in culture plates. After stimulating with preS-specific T cell peptide epitopes (Table 2) for 6 hr, the T cells were analysed for CD4, CD8 and INF-γ by FACS. The results of activated T cells were shown in FIG. 4. In mice immunized with preS VLP, $CD4^+$ and $CD8^+$ T cells were much higher than either the controls or those immunized with recombinant preS. The number of $CD8^+$ T cells or $CD4^+$ T cells coincides with that of $CD8^+$ T cells or $CD4^+$ T cells producing intracellular INF-γ. The secretion of INF-γ, which is considered to be a key in controlling and clearing HBV replication, was analysed by ELISPOT. The results showed that preS-specific INF-γ production is more abundant when mice were immunized with preS VLP (FIG. 4E). This suggests that preS VLP could evoke potent preS-specific $CD8^+$ T cells that are capable of HBV clearance.

Vaccination with preS VLP Offers Protection Against Challenge

Figure 5A:
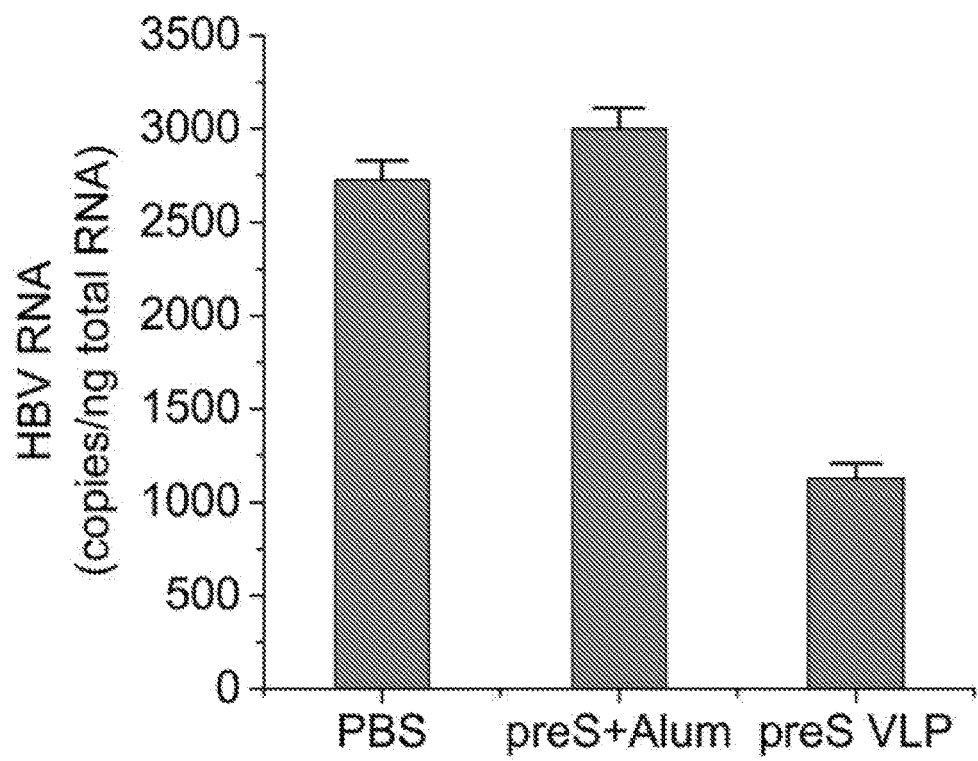
FIGS. 5A to 5F show vaccination with preS VLP offers protection against hydrodynamic HBV challenge. Balb/c mice were immunized intramuscularly with preS VLP (n=6), recombinant preS protein (n=6), or PBS (n=6). On day 70, HBV replication was induced by hydrodynamic injection of pT-HBV1.3 plasmid via tail vein (10 µg per mouse).
Figure 5B:
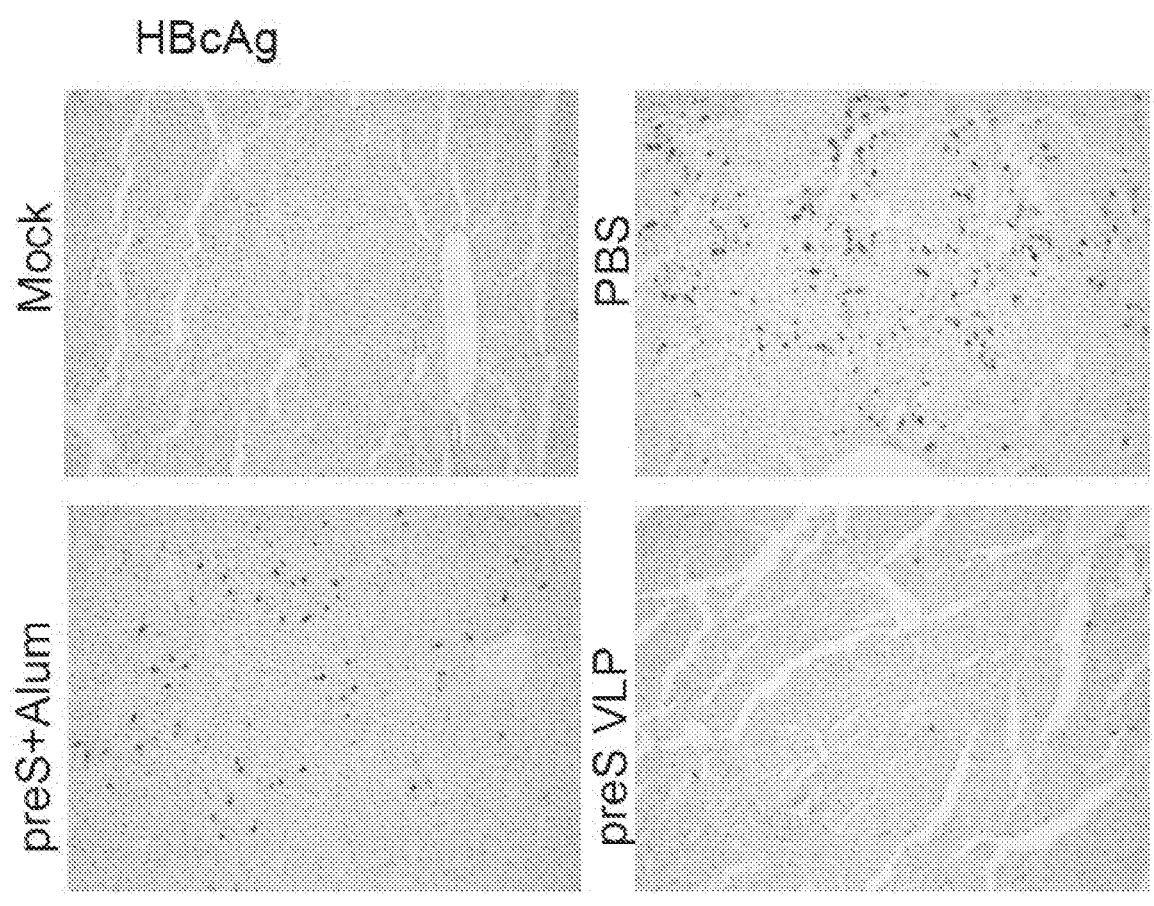
Figure 5C:
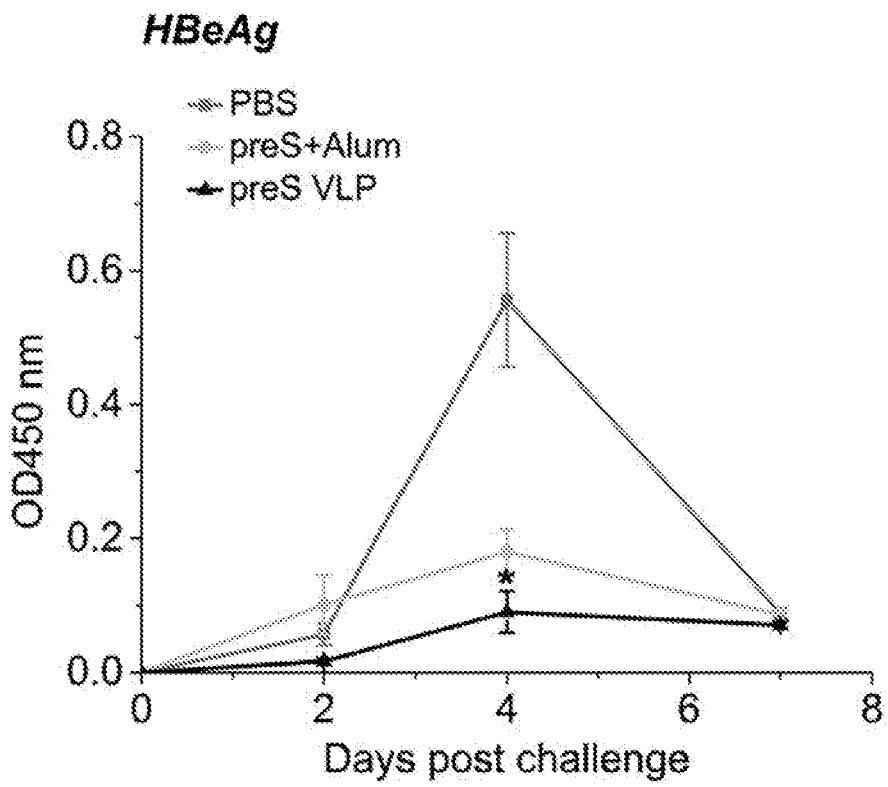
Figure 5D:
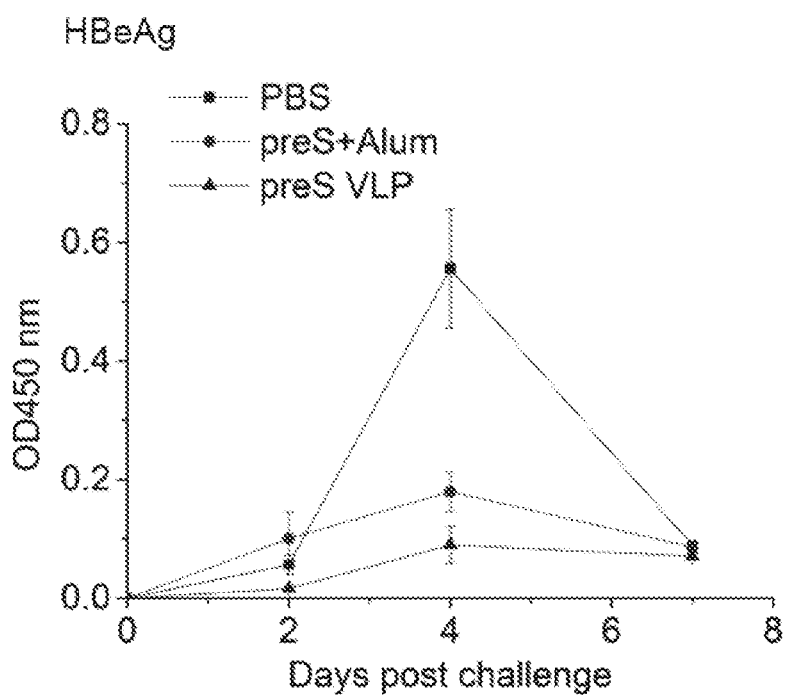
Figure 5E:
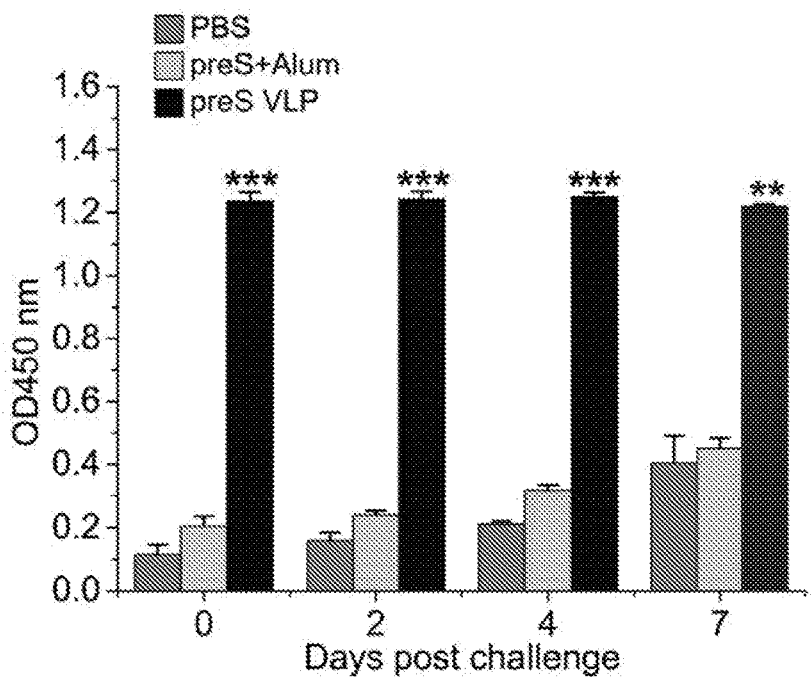
Figure 5F:
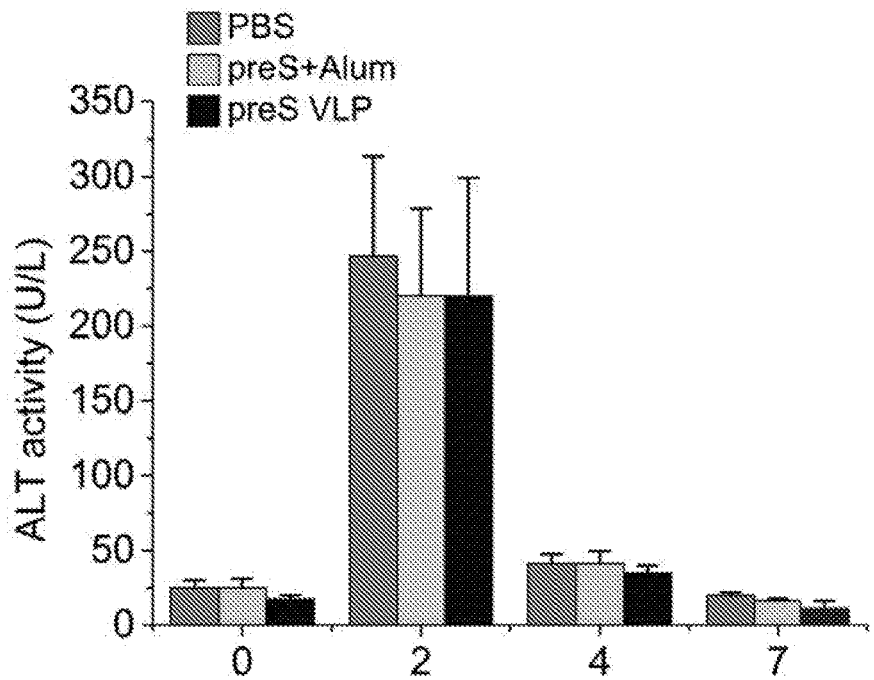

Immunized mice were challenged on day 70. HBV replication was induced by hydrodynamic injection of pT-HBV1.3 plasmid containing a 1.3-fold-overlength genome of HBV (10 μg). Liver tissues were collected on day 77 for HBV RNA detection, immunohistochemistry and T cell response analysis. HBV RNA copies were measured by qPCR (FIG. 5A). The levels of HBV RNA in preS VLP-immunized animals were significantly lower than that in animals immunized with recombinant preS. Liver sections stained for HBV core antigen indicated that HBcAg-positive hepatocytes in preS VLP-immunized animals eliminated almost entirely, while persisting at high levels in preS-immunized animals (FIG. 5B). A blood sample was collected from each mouse on day 70, 72, 74 and 77, and sera were prepared from these samples. HBsAg levels in preS VLP-immunized animals remained nearly undetectable through at least 7 days, while rising to high levels in animals immunized with recombinant preS on day 4 postchallenge (FIG. 5C). Levels of serum HBeAg also remained nearly undetectable in preS VLP-immunized animals over the course of 7 days. On the other hand, HBeAg levels in preS-immunized animals elevated on day 4 then dropped to nearly undetectable levels on day 7 postchallange (FIG. 5D). This phase of HBsAg and HBeAg clearance coincides with the development of anti-preS neutralizing antibodies (FIG. 5E). Thus, immunization with preS VLP controls and clears HBV replication within 7 days following HBV challenge by hydrodynamic injection of a 1.3-fold-overlength genome of HBV.

Protection Effect Correlates with Memory T Cell Responses

Figure 6A:
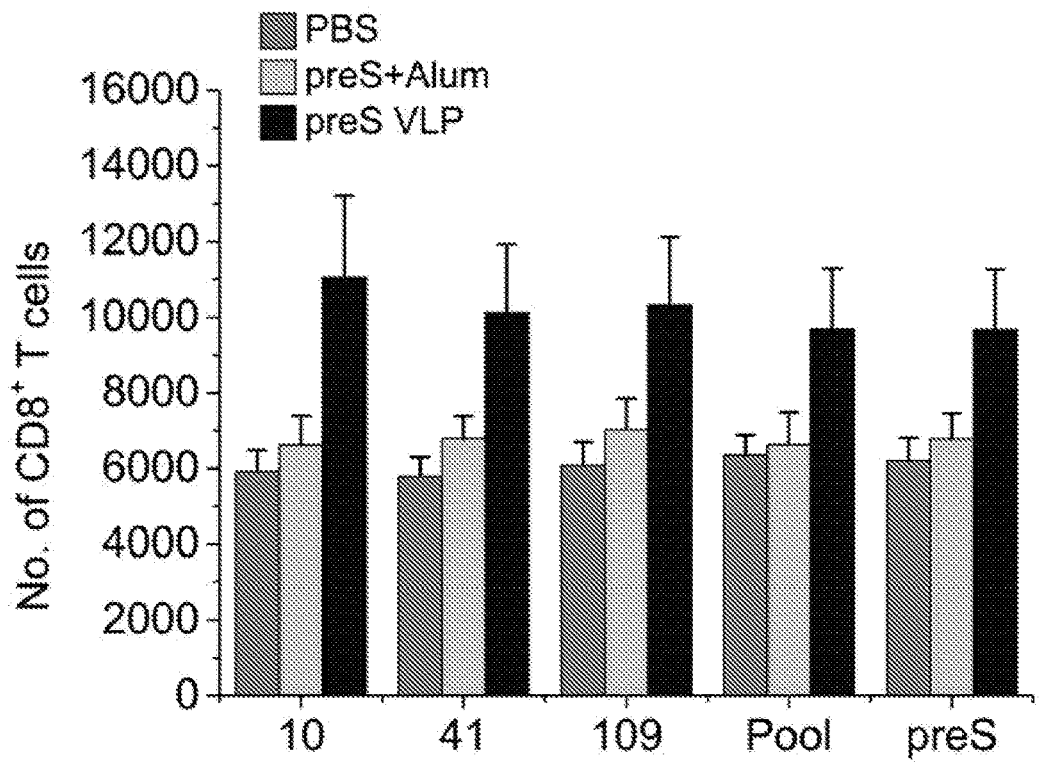
FIGS. 6A to 6F show preS VLP-mediated protection correlates with T cell recall response. Balb/c mice were immunized intramuscularly with preS VLP (n=6), recombinant preS protein (n=6), or PBS (n=6). On day 70, HBV replication was induced by hydrodynamic injection of pT-HBV1.3 plasmid (10 µg). 7 days postchallenge, splenocytes (FIGS. 6A-6E) and intrahepatic lymphocytes (FIG. 6F) were isolated and analyzed for CD8, CD4, and IFN-γ expression by flow cytometry (FIGS. 6A-6D) or ELISPOT assays (FIGS. 6E-6F).
Figure 6B:
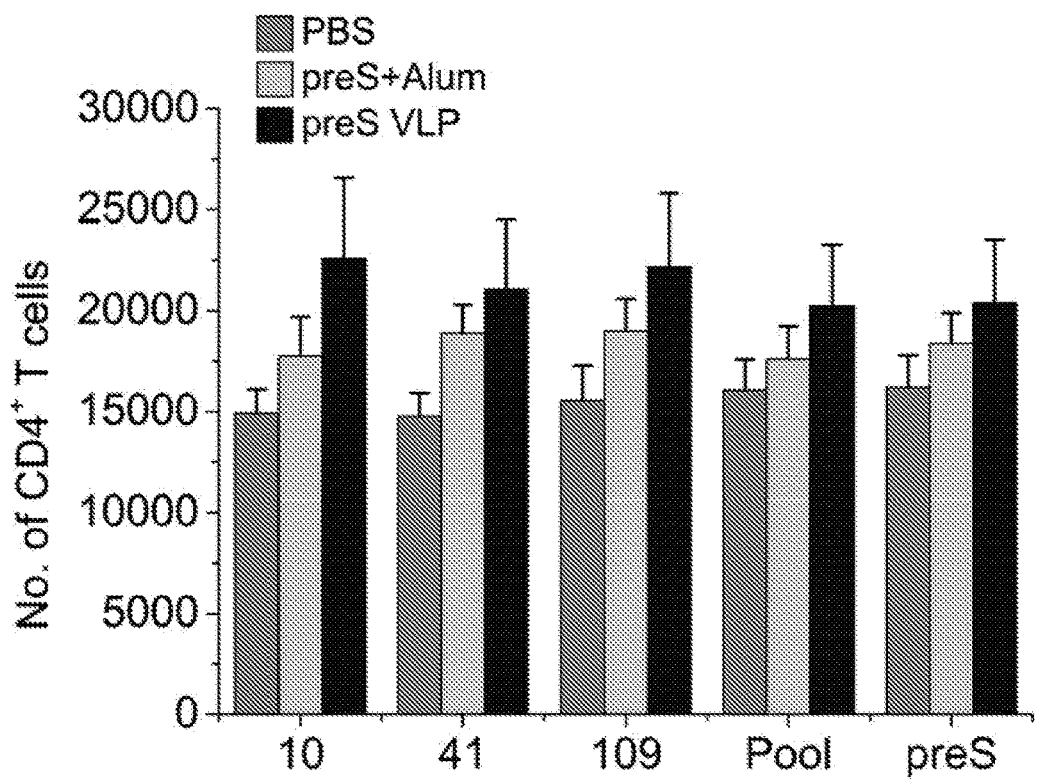
Figure 6C:
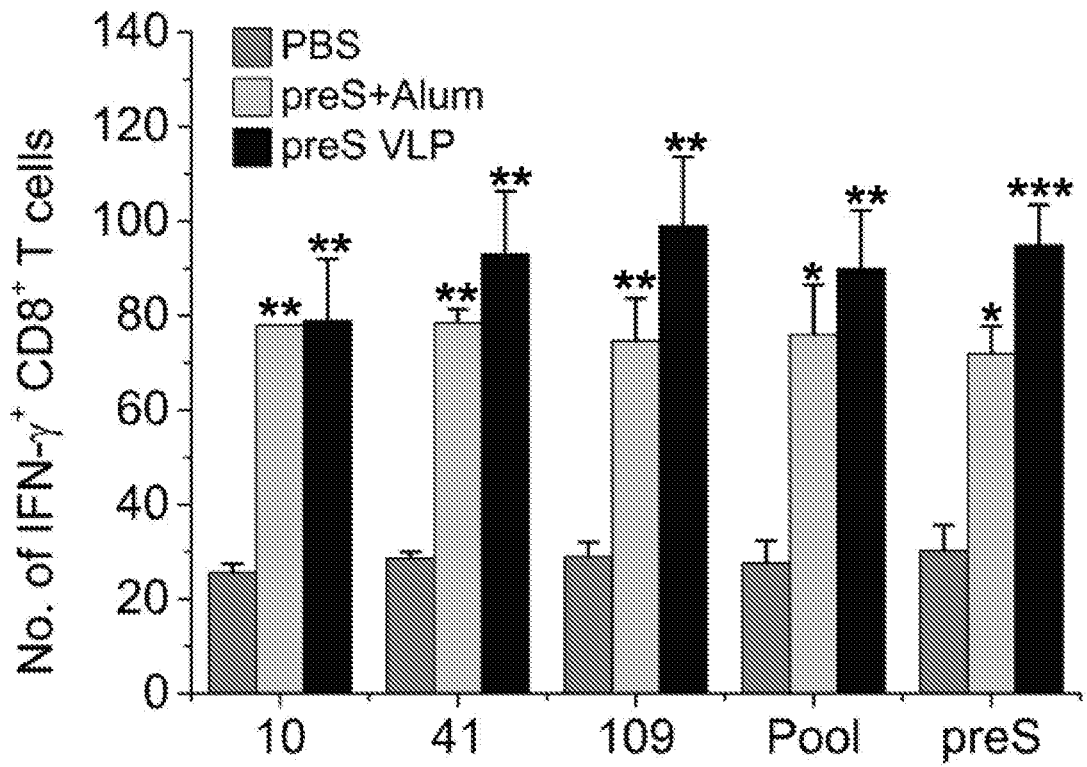
Figure 6D:
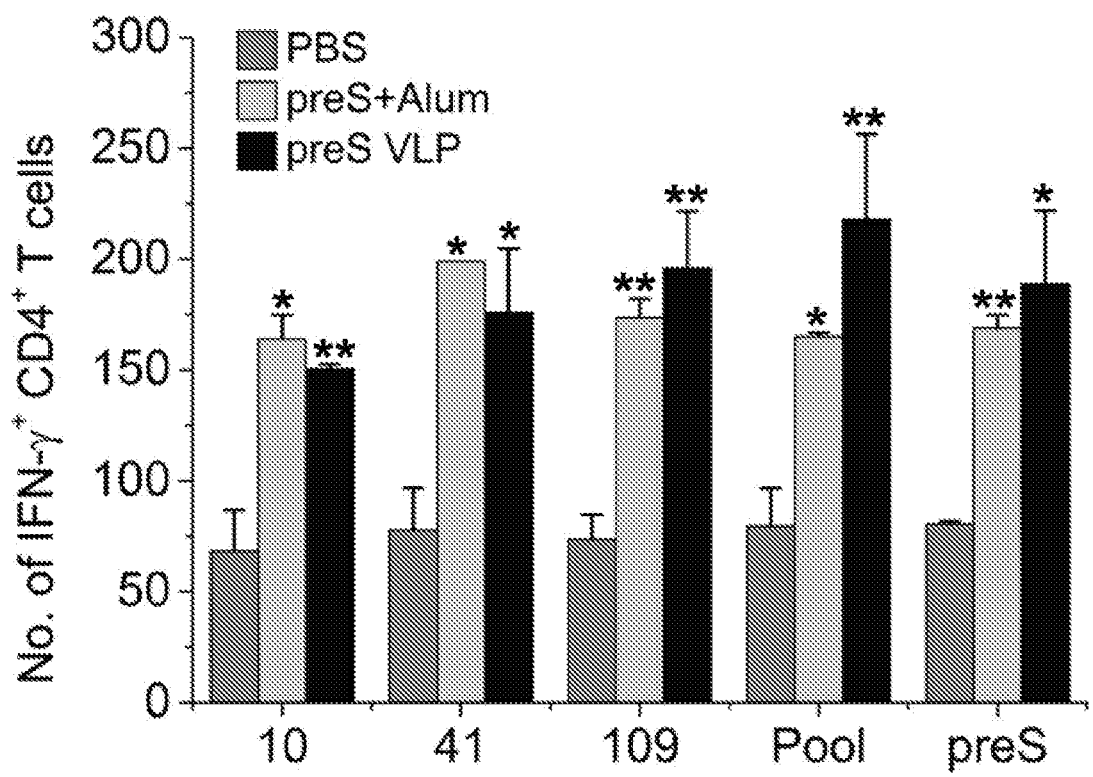
Figure 6E:
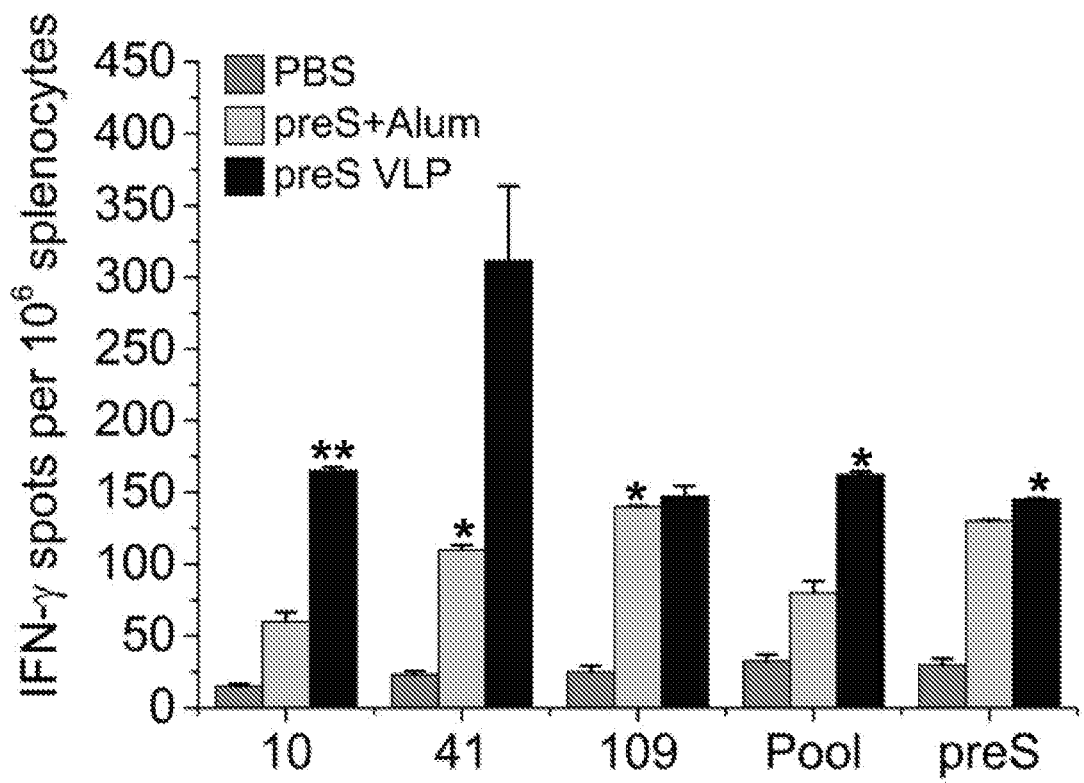
Figure 6F:
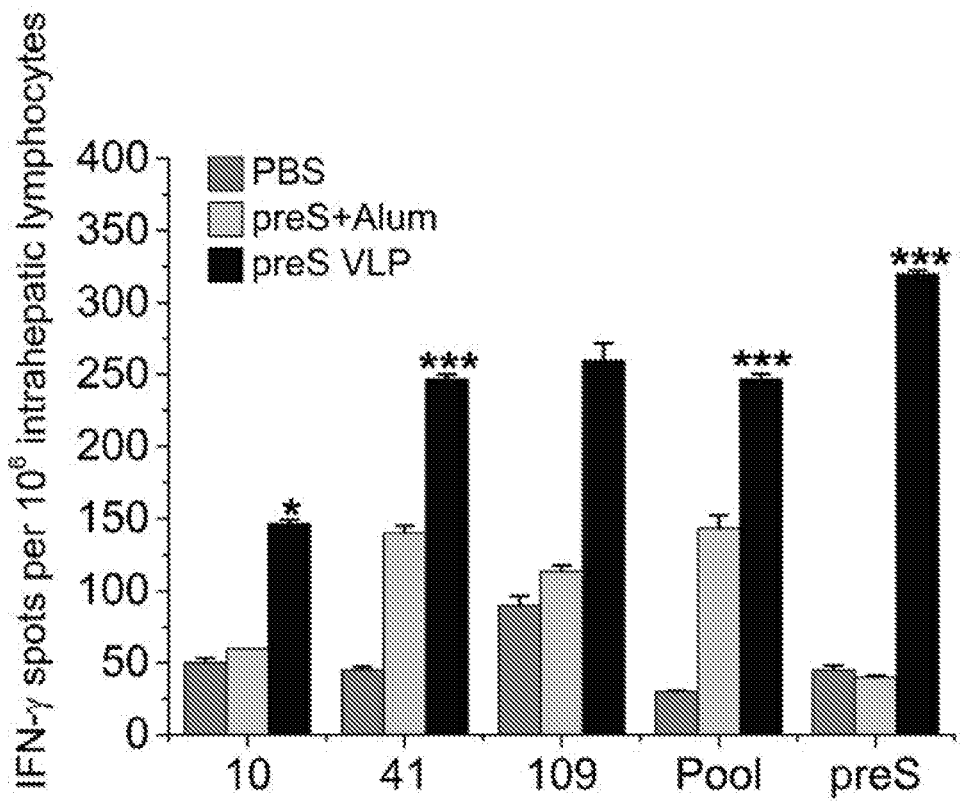

Since CD8 T cell responses would likely play an important role in HBV clearance, T cell recall responses in the spleen were analysed by FACS (FIG. 6A-D). In mice immunized with preS VLP, the number of CD8$^+$ and CD4$^+$ T cells was obviously higher than the controls and those immunized with recombinant preS, and the number of CD8$^+$ T cells or CD4$^+$ T cells producing intracellular INF-γ was also higher, but not as much. Notably, the number of CD8$^+$ T cells was significantly higher when mice were immunized with preS VLP, indicating that preS VLP induced memory T cells that could be recalled upon HBV challenge, and that the T cells were responsible for clearance of HBV. Furthermore, the T cell recall response was also measured by IFN-γ ELISPOT assays 7 days postchallenge on both splenocytes (FIG. 6E) and intrahepatic leukocytes (FIG. 6F). Interestingly, preS-specific T cell responses present in the liver and spleen of preS VLP-immunized mice were more potent than those in recombinant preS-immunized mice, suggesting that preS-specific T cells mediate clearance of HBV from transfected hepatocytes. Taken together, preS VLP elicits robust anti-preS neutralizing antibodies and preS-specific T cell responses, and could protect mice against HBV challenge, representing a novel prophylactic or potentially therapeutic vaccine candidate for HBV infection in humans.

Immune Responses in HBV Transgenic Mice

Figure 7D:
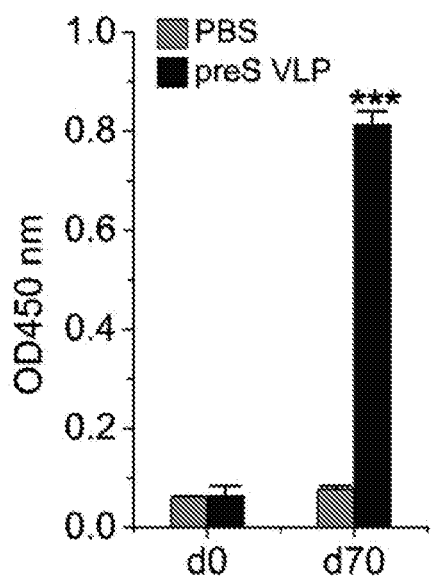
Figure 7E:
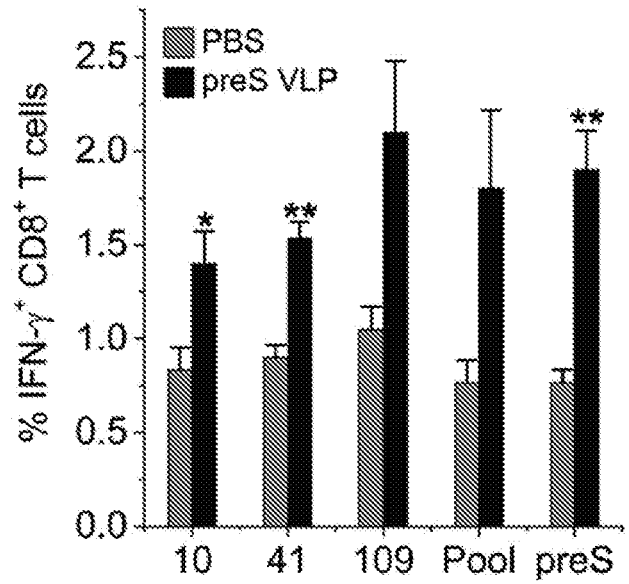
Figure 7F:
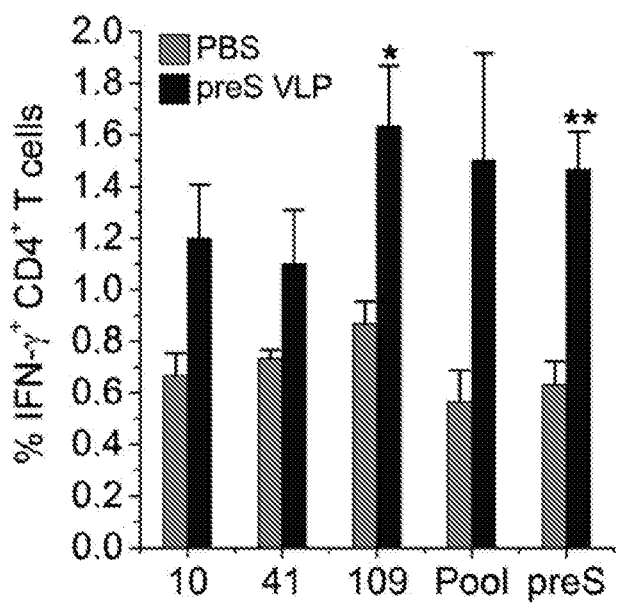
Figure 7G:
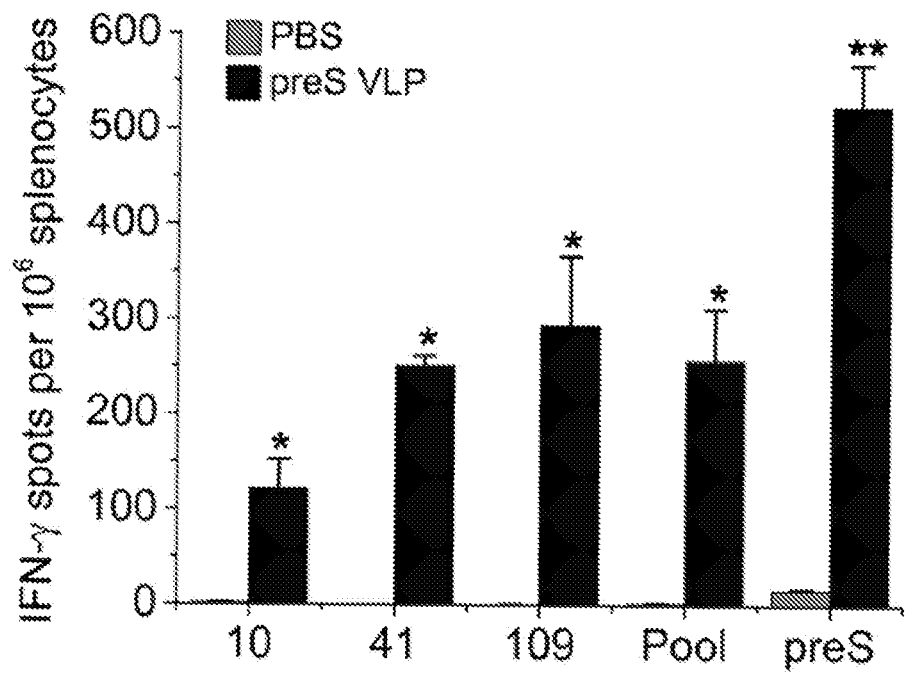
Figure 7H:
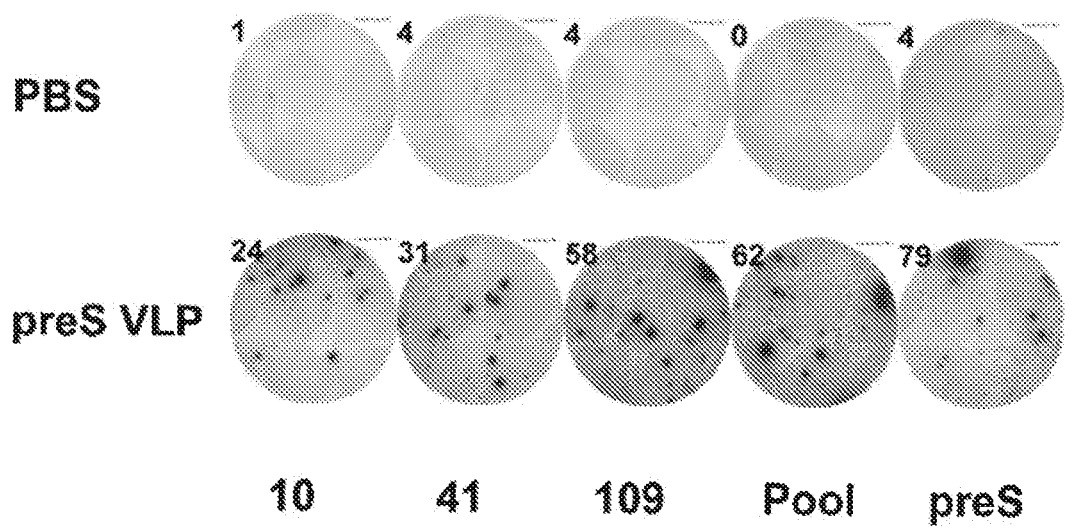
Figure 7I:
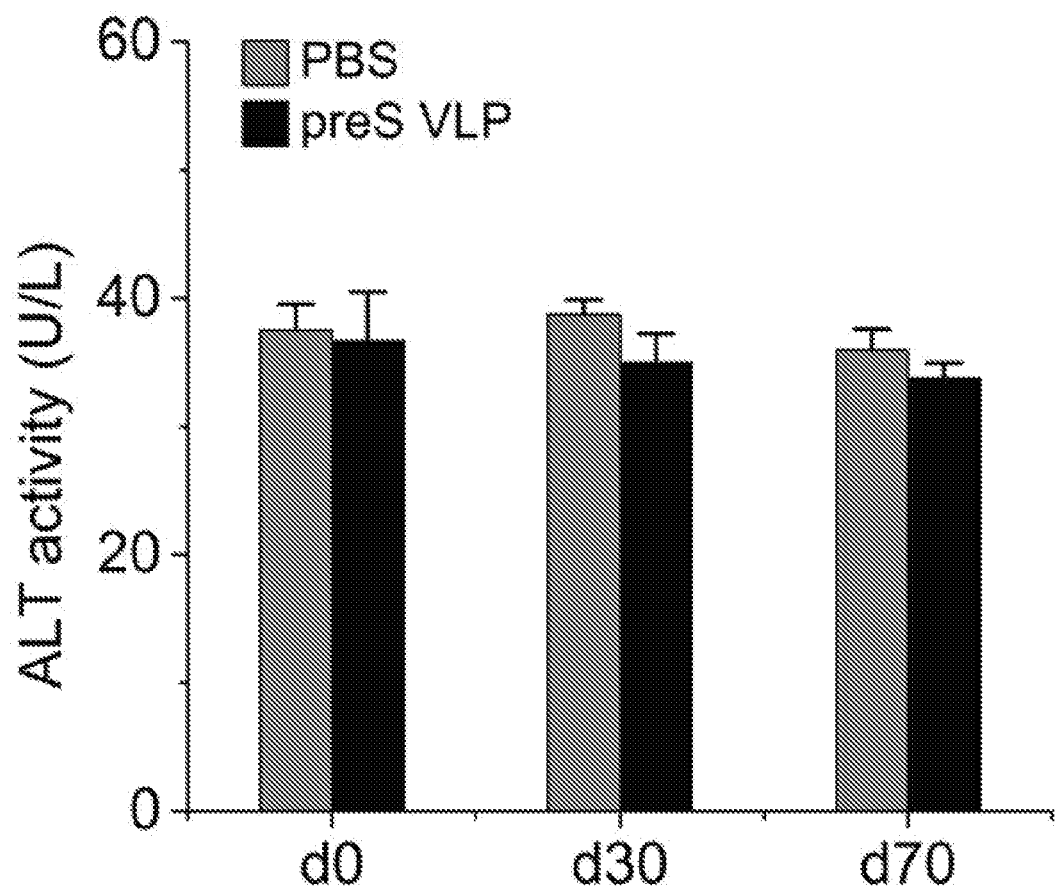
Figure 7J:
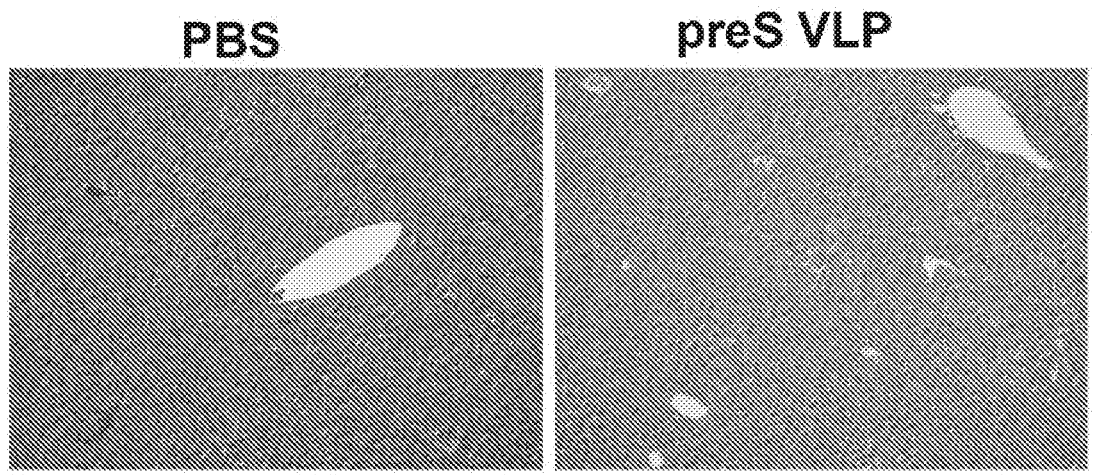

The therapeutic potential of preS VLP immunization was investigated by employing HBV transgenic mice as a model of chronic infection. HBV transgenic mice were first primed with preS VLP or PBS, and then were boosted on days 22 and 43, respectively. Despite that HBV transgenic mice have become tolerance to HBV (Allweiss L, Dandri M. J Hepatol 2016; 64:S17-31), preS VLP could still induce high levels of anti-preS total IgG including both anti-preS IgG1 (Th2 isotype) and IgG2a (Th1 isotype) (FIG. 7B-D), suggesting a balanced Th1/Th2 response against preS VLP. In addition, preS VLP immunization could also stimulate a higher percentage of preS-specific CD4+ and CD8+ T cells than either the control or recombinant preS immunization (FIGS. 7E, and 7F). Furthermore, preS-specific IFN-γ-producing T cells are more plentiful in mice immunized with preS VLP than either the controls or those immunized with recombinant preS protein (FIGS. 7G and 7H), implying the therapeutic potential of preS VLP. Taken together, preS VLP vaccine could induce preS-specific CD8+ and CD4+ T cell responses in HBV transgenic mice.

Discussion

Despite the success of currently available HBV S antigen-based vaccines, there are still 5-10% people do not respond adequately to provide protection against exposure to HBV (Kubba A K, et al. Commun Dis Public Health 2003 6:106-112). Due to the additional B and T cell epitopes in HBV preS region, preS represents an attractive antigen for HBV vaccine candidates that are able to overcome non-responsiveness to the S antigen-based vaccines (Grgacic E V, et al. Methods 2006 40:60-65). When combined with the S-antigen based vaccine, preS antigen may enhance the overall protection in a synergistic manner.

VLP-based vaccines are of high safety for lacking genetic material. Moreover, VLPs often display high immunogenicity because of presenting highly repetitive epitopes more similar to the native virus (Roldao A, et al. Expert Rev Vaccines 2010 9:1149-1176). Additionally, co-expression of influenza matrix protein M1 and hemagglutinin (HA) can self-assembly into virus-like particles (Galarza J M, et al. Viral Immunol 2005 18:244-251). This influenza VLP scaffold could be developed as a non-egg-based, cell culture-derived vaccine platform to present foreign antigens, such as HBV preS antigen (Lee D H, et al. Clin Exp Vaccine Res 2014 3:133-139).

A unique system has been successfully designed to produce a preS virus-like particle by co-expressing a M1 protein from influenza virus and a preS-HA chimeric protein. preS VLP in culture media may be purified by ultracentrifugation in a sucrose gradient. preS VLP is able to evoke much higher antibody titers than recombinant preS even without any adjuvants. This is likely due to the formation of HBV preS VLP, as this allows for endocytosis by antigen-presenting cells. Besides, the potential of preS VLP to elicit high antibody titers is most likely facilitated by highly repetitive preS antigen that is presented on the surface of the VLPs.

Anti-preS1 antibodies were previously found to be remarkably effective in neutralization of HBV (Neurath A R, et al. Vaccine 1989 7:234-236). The identification of protective epitopes within the preS1 region reveals that preS1 specific antibodies neutralize the virus by blocking the binding of host NTCP receptor (Yan H, et al. Elife 2012 1:e00049; Sankhyan A, et al. Sci Rep 2016 6:21240). These observations support the notion that an effective preS-based vaccine may expand the population of protected individuals. The disclosed results demonstrated that preS VLP can be an effective preS vaccine candidate. At the same time, as preS antigen is carried on the surface of VLP, class I antigen presentation pathway within the host cells can be exploited, resulting in potent T cell responses, which may also play a role in eliciting the high B cell responses. Furthermore, preS VLP are capable of protecting mice from HBV challenge, which may be probably due to the effective induction of B cell responses, and generation of memory CD8$^+$ T cells that are able to control infection.

The preS antigen has been exploited previously as candidates of prophylactic or therapeutic vaccines (Shouval D, et al. Med Microbiol Immunol 2015 204:57-68). When recombinant preS proteins were used in immunization, the antibody titers were not very high (Sylvan S P, et al. Vaccine 2009 28:446-451). The ability of neutralizing HBV by these antibodies is limited. More critically, no T cell responses against HBV were demonstrated (Raz R, et al. Vaccine 1996 14:207-211; Shapira M Y, et al. J Hepatol 2001 34:123-127). This is consistent with that isolated proteins generally do not induce T cell responses because they usually are not internalized by antigen presenting cells (Pennock N D, et al. Trends in immunology 2016 37:170-180). In order to overcome the barrier, virus or yeast vectors were employed to express HBV antigens (Sallberg M, et al. Human gene therapy 1998 9:1719-1729; Martin P, et al. Gut 2015 64:1961-1971; Reynolds T D, et al. Journal of virology 2015 89:10407-10415; King T H, et al. PloS one 2014 9:e101904). However, there are safety concerns when a replicating vector is used despite their capability to induce strong T cell responses. In addition, these vectors may only be given once because the host will establish immunity against the vector. The disclosed design of preS VLP has the advantages of mimicking the antigen surface of a virus particle and being able to enter the antigen presenting cells to elicit strong T cell responses, and at the same time, it permits multiple doses and does not replicate any foreign microorganism.

In conclusion, this preS VLP may be used as both prophylactic and therapeutic vaccines against hepatitis B virus infection in humans.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A virus like particle (VLP) comprising
   a) a fusion protein comprising
      i) a signal peptide,
      ii) a hepatitis B preS antigen,
      iii) a heterologous hemagglutinin (HA) transmembrane domain; and
   b) an influenza virus matrix protein 1 (M1),
   wherein the signal peptide is fused at the N-terminus of the hepatitis B preS antigen, wherein the hepatitis B preS antigen is fused at the N-terminus of the heterologous HA transmembrane domain, and
   wherein the preS antigen comprises the amino acid sequence SEQ ID NO:1, or an antigenic variant thereof having at least 90% identity to SEQ ID NO:1.

2. The VLP of claim 1, wherein the preS antigen comprises the amino acid sequence SEQ ID NO: 1.

3. The VLP of claim 1, wherein the fusion protein comprises the amino acid sequence SEQ ID NO:2.

4. The VLP of claim 1, wherein the signal peptide comprises the signal peptide from HA.

5. The VLP of claim 1, produced by coinfecting insect cells with one or more recombinant baculoviruses expressing the matrix protein and the fusion protein, culturing the insect cells under physiological conditions, and purifying the VLPs from insect cell culture supernatants.

6. The VLP of claim 5, produced by introducing into mammalian cells one or more expression vectors expressing the matrix protein and the fusion protein, culturing the mammalian cells under appropriate conditions, and purifying the VLPs from cell culture supernatants.

7. A vaccine comprising an effective amount of the VLP of claim 1 in a pharmaceutically acceptable excipient.

8. The vaccine of claim 7, further comprising an adjuvant.

9. A method of vaccinating a subject for hepatitis B comprising administering the vaccine of claim 7 to a subject in need thereof by intranasal, intramuscular, subcutaneous, transdermal, or sublingual administration.

10. The method of claim 9, further comprising administering to the subject a vaccine comprising a hepatitis B surface antigen (HBsAg).

11. A method for activating CD8+ T cells for adoptive cell therapy (ACT), comprising co-culturing CD8+ T cells and dendritic cells with the VLPs of claim 1.

12. The VLP of claim 1, wherein the heterologous HA further comprises a cytoplasmic tail.

13. The VLP of claim 12, wherein the heterologous HA comprises the amino acid sequence SEQ ID NO:15, or a variant thereof having at least 90% identity to SEQ ID NO:15.

\* \* \* \* \*

SEQUENCE LISTING

<160> NUMBER OF SEQ ID NOS: 125

<210> SEQ ID NO 1
<211> LENGTH: 163
<212> TYPE: PRT
<213> ORGANISM: Artificial Sequence
<220> FEATURE:
<223> OTHER INFORMATION: Synthetic Construct

<400> SEQUENCE: 1

Met Gly Thr Asn Leu Ser Val Pro Asn Pro Leu Gly Phe Phe Pro Asp
1               5                   10                  15

His Gln Leu Asp Pro Ala Phe Gly Ala Asn Ser Asn Asn Pro Asp Trp
            20                  25                  30

Asp Phe Asn Pro Ile Lys Asp His Trp Pro Ala Ala Asn Gln Val Gly
        35                  40                  45

Val Gly Ala Phe Gly Pro Gly Leu Thr Pro Pro His Gly Gly Ile Leu
    50                  55                  60

Gly Trp Ser Pro Gln Ala Gln Gly Ile Leu Thr Thr Val Ser Thr Ile
65                  70                  75                  80

Pro Pro Pro Ala Ser Thr Asn Arg Gln Ser Gly Arg Gln Pro Thr Pro
                85                  90                  95

Ile Ser Pro Pro Leu Arg Asp Ser His Pro Gln Ala Met Gln Trp Asn
            100                 105                 110

Ser Thr Ala Phe His Gln Ala Leu Gln Asp Pro Arg Val Arg Gly Leu
        115                 120                 125

Tyr Leu Pro Ala Gly Gly Ser Ser Ser Gly Thr Val Asn Pro Ala Pro
    130                 135                 140

Asn Ile Ala Ser His Ile Ser Ser Ile Ser Ala Arg Thr Gly Asp Pro
145                 150                 155                 160

Val Thr Asn

<210> SEQ ID NO 2
<211> LENGTH: 226
<212> TYPE: PRT
<213> ORGANISM: Artificial Sequence
<220> FEATURE:
<223> OTHER INFORMATION: Synthetic Construct

<400> SEQUENCE: 2

```
Met Glu Ala Lys Leu Phe Val Leu Phe Cys Ala Phe Thr Ala Leu Lys
1               5                   10                  15

Ala Met Gly Thr Asn Leu Ser Val Pro Asn Pro Leu Gly Phe Phe Pro
            20                  25                  30

Asp His Gln Leu Asp Pro Ala Phe Gly Ala Asn Ser Asn Asn Pro Asp
        35                  40                  45

Trp Asp Phe Asn Pro Ile Lys Asp His Trp Pro Ala Ala Asn Gln Val
    50                  55                  60

Gly Val Gly Ala Phe Gly Pro Gly Leu Thr Pro Pro His Gly Gly Ile
65                  70                  75                  80

Leu Gly Trp Ser Pro Gln Ala Gln Gly Ile Leu Thr Thr Val Ser Thr
                85                  90                  95

Ile Pro Pro Pro Ala Ser Thr Asn Arg Gln Ser Gly Arg Gln Pro Thr
            100                 105                 110

Pro Ile Ser Pro Pro Leu Arg Asp Ser His Pro Gln Ala Met Gln Trp
        115                 120                 125

Asn Ser Thr Ala Phe His Gln Ala Leu Gln Asp Pro Arg Val Arg Gly
    130                 135                 140

Leu Tyr Leu Pro Ala Gly Gly Ser Ser Ser Gly Thr Val Asn Pro Ala
145                 150                 155                 160

Pro Asn Ile Ala Ser His Ile Ser Ser Ile Ser Ala Arg Thr Gly Asp
                165                 170                 175

Pro Val Thr Asn Lys Leu Glu Ser Val Gly Val His Gln Ile Leu Ala
            180                 185                 190

Ile Tyr Ser Thr Val Ala Ser Ser Leu Val Leu Leu Val Ser Leu Gly
        195                 200                 205

Ala Ile Ser Phe Trp Met Cys Ser Asn Gly Ser Leu Gln Cys Arg Ile
    210                 215                 220

Cys Ile
225
```

```
<210> SEQ ID NO 3
<211> LENGTH: 252
<212> TYPE: PRT
<213> ORGANISM: Artificial Sequence
<220> FEATURE:
<223> OTHER INFORMATION: Synthetic Construct
```

<400> SEQUENCE: 3

```
Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Gly Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ser Leu Ser Tyr Ser Thr Gly Ala Leu Ala Ser Cys Met
```

-continued

```
                    115                 120                 125
Gly Leu Ile Tyr Asn Arg Met Gly Thr Val Thr Thr Glu Ala Ala Phe
    130                 135                 140
Gly Leu Val Cys Ala Thr Cys Glu Gln Ile Ala Asp Ser Gln His Arg
145                 150                 155                 160
Ser His Arg Gln Met Ala Thr Thr Asn Pro Leu Ile Arg His Glu
                165                 170                 175
Asn Arg Met Val Leu Ala Ser Thr Thr Ala Lys Ala Met Glu Gln Met
            180                 185                 190
Ala Gly Ser Ser Glu Gln Ala Ala Glu Ala Met Glu Val Ala Ser Gln
        195                 200                 205
Thr Arg Gln Met Val His Ala Met Arg Thr Ile Gly Thr His Pro Ser
    210                 215                 220
Ser Ser Ala Gly Leu Lys Asp Asp Leu Leu Glu Asn Leu Gln Ala Tyr
225                 230                 235                 240
Gln Lys Arg Met Gly Val Gln Ile Gln Arg Phe Lys
                245                 250

<210> SEQ ID NO 4
<211> LENGTH: 16
<212> TYPE: DNA
<213> ORGANISM: Artificial Sequence
<220> FEATURE:
<223> OTHER INFORMATION: Synthetic Construct

<400> SEQUENCE: 4
ccaccaatcg gcagtc                                                      16

<210> SEQ ID NO 5
<211> LENGTH: 17
<212> TYPE: DNA
<213> ORGANISM: Artificial Sequence
<220> FEATURE:
<223> OTHER INFORMATION: Synthetic Construct

<400> SEQUENCE: 5
gccaccagca ggaagat                                                     17

<210> SEQ ID NO 6
<211> LENGTH: 19
<212> TYPE: DNA
<213> ORGANISM: Artificial Sequence
<220> FEATURE:
<223> OTHER INFORMATION: Synthetic Construct

<400> SEQUENCE: 6
tgacaacaac caacccact                                                   19

<210> SEQ ID NO 7
<211> LENGTH: 18
<212> TYPE: DNA
<213> ORGANISM: Artificial Sequence
<220> FEATURE:
<223> OTHER INFORMATION: Synthetic Construct

<400> SEQUENCE: 7
ctgctgcttg ctcactcg                                                    18

<210> SEQ ID NO 8
<211> LENGTH: 23
<212> TYPE: DNA
<213> ORGANISM: Artificial Sequence
```

```
<220> FEATURE:
<223> OTHER INFORMATION: Synthetic Construct

<400> SEQUENCE: 8
tcatgaagtg tgacgtggac atc                                              23

<210> SEQ ID NO 9
<211> LENGTH: 24
<212> TYPE: DNA
<213> ORGANISM: Artificial Sequence
<220> FEATURE:
<223> OTHER INFORMATION: Synthetic Construct

<400> SEQUENCE: 9
caggaggagc aatgatcttg atct                                             24

<210> SEQ ID NO 10
<211> LENGTH: 19
<212> TYPE: DNA
<213> ORGANISM: Artificial Sequence
<220> FEATURE:
<223> OTHER INFORMATION: Synthetic Construct

<400> SEQUENCE: 10
gagtgtggat tcgcactcc                                                   19

<210> SEQ ID NO 11
<211> LENGTH: 19
<212> TYPE: DNA
<213> ORGANISM: Artificial Sequence
<220> FEATURE:
<223> OTHER INFORMATION: Synthetic Construct

<400> SEQUENCE: 11
gaggcgaggg agttcttct                                                   19

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Pro Leu Gly Phe Phe Pro Asp His Gln Leu
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Synthetic Construct

<400> SEQUENCE: 13

Trp Pro Ala Ala Asn Gln Val Gly Val Gly Ala Phe Gly Pro Gly Leu
1               5                   10                  15

<210> SEQ ID NO 14
<211> LENGTH: 26
<212> TYPE: PRT
<213> ORGANISM: Artificial Sequence
<220> FEATURE:
<223> OTHER INFORMATION: Synthetic Construct

<400> SEQUENCE: 14
```

Met Gln Trp Asn Ser Thr Ala Phe His Gln Ala Leu Gln Asp Pro Arg
1               5                   10                  15

Val Arg Gly Leu Tyr Leu Pro Ala Gly Gly
            20                  25

<210> SEQ ID NO 15
<211> LENGTH: 46
<212> TYPE: PRT
<213> ORGANISM: Artificial Sequence
<220> FEATURE:
<223> OTHER INFORMATION: Synthetic Construct

<400> SEQUENCE: 15

Lys Leu Glu Ser Val Gly Val His Gln Ile Leu Ala Ile Tyr Ser Thr
1               5                   10                  15

Val Ala Ser Ser Leu Val Leu Leu Val Ser Leu Gly Ala Ile Ser Phe
            20                  25                  30

Trp Met Cys Ser Asn Gly Ser Leu Gln Cys Arg Ile Cys Ile
            35                  40                  45

<210> SEQ ID NO 16
<211> LENGTH: 17
<212> TYPE: PRT
<213> ORGANISM: Artificial Sequence
<220> FEATURE:
<223> OTHER INFORMATION: Synthetic Construct

<400> SEQUENCE: 16

Met Glu Ala Lys Leu Phe Val Leu Phe Cys Ala Phe Thr Ala Leu Lys
1               5                   10                  15

Ala

<210> SEQ ID NO 17
<211> LENGTH: 12
<212> TYPE: PRT
<213> ORGANISM: Artificial Sequence
<220> FEATURE:
<223> OTHER INFORMATION: Synthetic Construct

<400> SEQUENCE: 17

Val Leu Leu Leu Ala Ile Val Ser Leu Val Lys Ser
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Synthetic Construct

<400> SEQUENCE: 18

Met Glu Arg Ile Val Ile Ala Leu Ala Ile Ile Ser Val Val Lys Gly
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: Synthetic Construct

<400> SEQUENCE: 19

Met Glu Lys Phe Ile Ile Leu Ser Thr Val Leu Ala Ala Ser Phe Ala
1               5                   10                  15

Tyr

<210> SEQ ID NO 20
<211> LENGTH: 18
<212> TYPE: PRT
<213> ORGANISM: Artificial Sequence
<220> FEATURE:
<223> OTHER INFORMATION: Synthetic Construct

<400> SEQUENCE: 20

Met Asn Thr Gln Ile Leu Val Phe Ile Ala Cys Val Leu Ile Glu Ala
1               5                   10                  15

Lys Gly

<210> SEQ ID NO 21
<211> LENGTH: 18
<212> TYPE: PRT
<213> ORGANISM: Artificial Sequence
<220> FEATURE:
<223> OTHER INFORMATION: Synthetic Construct

<400> SEQUENCE: 21

Met Asn Thr Gln Ile Leu Ile Leu Thr Leu Val Ala Ala Ile His Thr
1               5                   10                  15

Asn Ala

<210> SEQ ID NO 22
<211> LENGTH: 16
<212> TYPE: PRT
<213> ORGANISM: Artificial Sequence
<220> FEATURE:
<223> OTHER INFORMATION: Synthetic Construct

<400> SEQUENCE: 22

Met Ala Arg Leu Pro Ile Leu Leu Leu Ile Ser Leu Val Tyr Ser
1               5                   10                  15

<210> SEQ ID NO 23
<211> LENGTH: 18
<212> TYPE: PRT
<213> ORGANISM: Artificial Sequence
<220> FEATURE:
<223> OTHER INFORMATION: Synthetic Construct

<400> SEQUENCE: 23

Met Asn Thr Gln Ile Leu Val Phe Ala Leu Val Ala Val Ile Pro Thr
1               5                   10                  15

Asn Ala

<210> SEQ ID NO 24
<211> LENGTH: 16
<212> TYPE: PRT
<213> ORGANISM: Artificial Sequence
<220> FEATURE:
<223> OTHER INFORMATION: Synthetic Construct

<400> SEQUENCE: 24

Met Lys Thr Ile Ile Ala Leu Ser Tyr Ile Phe Cys Leu Ala Leu Gly
1               5                   10                  15

<210> SEQ ID NO 25
<211> LENGTH: 16
<212> TYPE: PRT
<213> ORGANISM: Artificial Sequence
<220> FEATURE:

<223> OTHER INFORMATION: Synthetic Construct

<400> SEQUENCE: 25

Met Lys Lys Val Leu Leu Phe Ala Ala Ile Ile Cys Ile Arg Ala
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic Construct

<400> SEQUENCE: 26

Met Lys Thr Thr Ile Ile Leu Ile Leu Leu Thr His Trp Val Tyr Ser
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Synthetic Construct

<400> SEQUENCE: 27

Met Lys Thr Thr Ile Val Leu Ile Leu Leu Thr His Trp Val Tyr Ser
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic Construct

<400> SEQUENCE: 28

Met Lys Ala Ile Ile Val Leu Leu Met Val Val Thr Ser Asn Ala
1               5                   10                  15

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Ser Leu Val Lys Ser
1               5

<210> SEQ ID NO 30
<211> LENGTH: 16
<212> TYPE: PRT
<213> ORGANISM: Artificial Sequence
<220> FEATURE:
<223> OTHER INFORMATION: Synthetic Construct

<400> SEQUENCE: 30

Met Glu Lys Thr Leu Leu Phe Ala Ala Ile Phe Leu Cys Val Lys Ala
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Synthetic Construct

<400> SEQUENCE: 31

Met Lys Thr Ile Ile Ala Leu Ser Tyr Ile Phe Cys Leu Val Leu Gly
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Synthetic Construct

<400> SEQUENCE: 32

Met Lys Thr Ile Ile Val Leu Ser Cys Phe Phe Cys Leu Ala Phe Ser
1               5                   10                  15

<210> SEQ ID NO 33
<211> LENGTH: 18
<212> TYPE: PRT
<213> ORGANISM: Artificial Sequence
<220> FEATURE:
<223> OTHER INFORMATION: Synthetic Construct

<400> SEQUENCE: 33

Met Asp Ile Arg Pro Ile Ile Ile Ser Leu Leu Ile Ser Thr Cys Val
1               5                   10                  15

Gln Ala

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

<400> SEQUENCE: 34

Leu Met Val Val Thr Ser Asn Ala
1               5

<210> SEQ ID NO 35
<211> LENGTH: 11
<212> TYPE: PRT
<213> ORGANISM: Artificial Sequence
<220> FEATURE:
<223> OTHER INFORMATION: Synthetic Construct

<400> SEQUENCE: 35

Ile Val Leu Leu Met Val Val Thr Ser Asn Ala
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Ala Ile Val Ser Leu Val Lys Ser
1               5

<210> SEQ ID NO 37
<211> LENGTH: 18
<212> TYPE: PRT
<213> ORGANISM: Artificial Sequence
<220> FEATURE:

```
<223> OTHER INFORMATION: Synthetic Construct

<400> SEQUENCE: 37

Met Asn Thr Gln Ile Leu Ile Leu Ala Thr Ser Ala Phe Leu Cys Val
1               5                   10                  15

Arg Ala

<210> SEQ ID NO 38
<211> LENGTH: 16
<212> TYPE: PRT
<213> ORGANISM: Artificial Sequence
<220> FEATURE:
<223> OTHER INFORMATION: Synthetic Construct

<400> SEQUENCE: 38

Met Leu Ser Ile Thr Ile Leu Phe Leu Leu Ile Ala Glu Gly Ser Ser
1               5                   10                  15

<210> SEQ ID NO 39
<211> LENGTH: 17
<212> TYPE: PRT
<213> ORGANISM: Artificial Sequence
<220> FEATURE:
<223> OTHER INFORMATION: Synthetic Construct

<400> SEQUENCE: 39

Met Glu Ala Lys Leu Leu Val Leu Phe Cys Thr Phe Ala Ala Leu Lys
1               5                   10                  15

Ala

<210> SEQ ID NO 40
<211> LENGTH: 16
<212> TYPE: PRT
<213> ORGANISM: Artificial Sequence
<220> FEATURE:
<223> OTHER INFORMATION: Synthetic Construct

<400> SEQUENCE: 40

Met Thr Arg Leu Pro Ile Leu Leu Leu Ile Ser Leu Val Tyr Ala
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Synthetic Construct

<400> SEQUENCE: 41

Met Leu Ser Ile Val Ile Leu Phe Leu Leu Ile Ala Glu Asn Ser Ser
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic Construct

<400> SEQUENCE: 42

Met Lys Thr Thr Ile Ile Leu Ile Leu Leu Ile His Trp Val His Ser
1               5                   10                  15

<210> SEQ ID NO 43
<211> LENGTH: 21
```

<212> TYPE: PRT
<213> ORGANISM: Artificial Sequence
<220> FEATURE:
<223> OTHER INFORMATION: Synthetic Construct

<400> SEQUENCE: 43

Met Leu Ser Leu Ile Met Arg Thr Val Ile Ala Leu Ser Tyr Ile Phe
1               5                   10                  15

Cys Leu Ala Phe Gly
            20

<210> SEQ ID NO 44
<211> LENGTH: 16
<212> TYPE: PRT
<213> ORGANISM: Artificial Sequence
<220> FEATURE:
<223> OTHER INFORMATION: Synthetic Construct

<400> SEQUENCE: 44

Met Glu Lys Ile Val Leu Leu Leu Ala Ile Val Ser Leu Val Lys Ser
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetic Construct

<400> SEQUENCE: 45

Met Lys Thr Thr Thr Ile Leu Ile Leu Leu Thr His Trp Val His Ser
1               5                   10                  15

<210> SEQ ID NO 46
<211> LENGTH: 17
<212> TYPE: PRT
<213> ORGANISM: Artificial Sequence
<220> FEATURE:
<223> OTHER INFORMATION: Synthetic Construct

<400> SEQUENCE: 46

Met Lys Ala Lys Leu Leu Val Leu Leu Cys Ala Leu Ser Ala Thr Asp
1               5                   10                  15

Ala

<210> SEQ ID NO 47
<211> LENGTH: 15
<212> TYPE: PRT
<213> ORGANISM: Artificial Sequence
<220> FEATURE:
<223> OTHER INFORMATION: Synthetic Construct

<400> SEQUENCE: 47

Met Ala Ile Ile Tyr Leu Ile Leu Leu Phe Thr Ala Val Arg Gly
1               5                   10                  15

<210> SEQ ID NO 48
<211> LENGTH: 18
<212> TYPE: PRT
<213> ORGANISM: Artificial Sequence
<220> FEATURE:
<223> OTHER INFORMATION: Synthetic Construct

<400> SEQUENCE: 48

Met Asn Thr Gln Ile Leu Ile Leu Ala Ile Ser Ala Phe Leu Cys Val
1               5                   10                  15

Arg Ala

<210> SEQ ID NO 49
<211> LENGTH: 16
<212> TYPE: PRT
<213> ORGANISM: Artificial Sequence
<220> FEATURE:
<223> OTHER INFORMATION: Synthetic Construct

<400> SEQUENCE: 49

Met Glu Glu Ile Val Leu Leu Phe Ala Ile Val Ser Leu Ala Arg Ser
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic Construct

<400> SEQUENCE: 50

Met Glu Lys Ile Val Leu Leu Leu Ala Thr Val Ser Leu Val Lys Ser
1               5                   10                  15

<210> SEQ ID NO 51
<211> LENGTH: 17
<212> TYPE: PRT
<213> ORGANISM: Artificial Sequence
<220> FEATURE:
<223> OTHER INFORMATION: Synthetic Construct

<400> SEQUENCE: 51

Met Lys Ala Lys Leu Leu Val Leu Leu Tyr Ala Phe Val Ala Thr Asp
1               5                   10                  15

Ala

<210> SEQ ID NO 52
<211> LENGTH: 18
<212> TYPE: PRT
<213> ORGANISM: Artificial Sequence
<220> FEATURE:
<223> OTHER INFORMATION: Synthetic Construct

<400> SEQUENCE: 52

Met Asp Ile Arg Ala Ile Val Ile Ser Leu Leu Ile Ser Thr Cys Val
1               5                   10                  15

Gln Ala

<210> SEQ ID NO 53
<211> LENGTH: 16
<212> TYPE: PRT
<213> ORGANISM: Artificial Sequence
<220> FEATURE:
<223> OTHER INFORMATION: Synthetic Construct

<400> SEQUENCE: 53

Met Glu Arg Ile Val Ile Ala Leu Ala Ile Ile Asn Ile Val Lys Gly
1               5                   10                  15

<210> SEQ ID NO 54
<211> LENGTH: 17
<212> TYPE: PRT
<213> ORGANISM: Artificial Sequence
<220> FEATURE:
<223> OTHER INFORMATION: Synthetic Construct

<400> SEQUENCE: 54

Met Glu Ala Lys Leu Phe Val Leu Phe Cys Thr Phe Thr Val Leu Lys
1               5                   10                  15

Ala

<210> SEQ ID NO 55
<211> LENGTH: 16
<212> TYPE: PRT
<213> ORGANISM: Artificial Sequence
<220> FEATURE:
<223> OTHER INFORMATION: Synthetic Construct

<400> SEQUENCE: 55

Met Lys Thr Ile Ile Ala Leu Ser Tyr Ile Phe Cys Leu Ala Phe Ser
1               5                   10                  15

<210> SEQ ID NO 56
<211> LENGTH: 17
<212> TYPE: PRT
<213> ORGANISM: Artificial Sequence
<220> FEATURE:
<223> OTHER INFORMATION: Synthetic Construct

<400> SEQUENCE: 56

Met Lys Ala Lys Leu Leu Val Leu Leu Cys Ala Phe Thr Ala Thr Asp
1               5                   10                  15

Ala

<210> SEQ ID NO 57
<211> LENGTH: 16
<212> TYPE: PRT
<213> ORGANISM: Artificial Sequence
<220> FEATURE:
<223> OTHER INFORMATION: Synthetic Construct

<400> SEQUENCE: 57

Met Thr Arg Leu Ser Ile Leu Leu Leu Ile Ser Leu Val Tyr Ser
1               5                   10                  15

<210> SEQ ID NO 58
<211> LENGTH: 17
<212> TYPE: PRT
<213> ORGANISM: Artificial Sequence
<220> FEATURE:
<223> OTHER INFORMATION: Synthetic Construct

<400> SEQUENCE: 58

Met Glu Ala Arg Leu Leu Val Leu Leu Cys Ala Phe Ala Ala Thr Asn
1               5                   10                  15

Ala

<210> SEQ ID NO 59
<211> LENGTH: 16
<212> TYPE: PRT
<213> ORGANISM: Artificial Sequence
<220> FEATURE:
<223> OTHER INFORMATION: Synthetic Construct

<400> SEQUENCE: 59

Met Glu Lys Phe Ile Ala Ile Ala Thr Leu Ala Ser Thr Asn Ala Tyr
1               5                   10                  15

<210> SEQ ID NO 60

```
<211> LENGTH: 17
<212> TYPE: PRT
<213> ORGANISM: Artificial Sequence
<220> FEATURE:
<223> OTHER INFORMATION: Synthetic Construct

<400> SEQUENCE: 60

Met Lys Ala Ile Leu Leu Val Leu Leu Cys Ala Phe Ala Ala Thr Asn
1               5                   10                  15

Ala

<210> SEQ ID NO 61
<211> LENGTH: 16
<212> TYPE: PRT
<213> ORGANISM: Artificial Sequence
<220> FEATURE:
<223> OTHER INFORMATION: Synthetic Construct

<400> SEQUENCE: 61

Met Lys Thr Ile Ile Ala Leu Ser Tyr Ile Phe Cys Leu Ala Phe Ala
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Synthetic Construct

<400> SEQUENCE: 62

Met Lys Thr Ile Ile Ala Leu Ser Tyr Ile Phe Cys Gln Val Phe Ala
1               5                   10                  15

<210> SEQ ID NO 63
<211> LENGTH: 18
<212> TYPE: PRT
<213> ORGANISM: Artificial Sequence
<220> FEATURE:
<223> OTHER INFORMATION: Synthetic Construct

<400> SEQUENCE: 63

Met Asp Ile Gln Ala Val Ala Leu Leu Ile Leu Thr Ser Thr Cys Val
1               5                   10                  15

Gln Ala

<210> SEQ ID NO 64
<211> LENGTH: 16
<212> TYPE: PRT
<213> ORGANISM: Artificial Sequence
<220> FEATURE:
<223> OTHER INFORMATION: Synthetic Construct

<400> SEQUENCE: 64

Met Lys Gln Leu Ser Ile Val Ile Leu Leu Ser Ile Val Tyr Thr
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic Construct

<400> SEQUENCE: 65

Met Thr Ile Thr Phe Leu Ile Leu Leu Phe Thr Val Val Lys Gly
1               5                   10                  15
```

<210> SEQ ID NO 66
<211> LENGTH: 16
<212> TYPE: PRT
<213> ORGANISM: Artificial Sequence
<220> FEATURE:
<223> OTHER INFORMATION: Synthetic Construct

<400> SEQUENCE: 66

Met Lys Thr Ile Ile Ala Leu Ser Tyr Ile Phe Cys Leu Val Phe Ala
1               5                   10                  15

<210> SEQ ID NO 67
<211> LENGTH: 18
<212> TYPE: PRT
<213> ORGANISM: Artificial Sequence
<220> FEATURE:
<223> OTHER INFORMATION: Synthetic Construct

<400> SEQUENCE: 67

Met Ala Leu Asn Val Ile Ala Thr Leu Thr Leu Ile Ser Val Cys Val
1               5                   10                  15

His Ala

<210> SEQ ID NO 68
<211> LENGTH: 16
<212> TYPE: PRT
<213> ORGANISM: Artificial Sequence
<220> FEATURE:
<223> OTHER INFORMATION: Synthetic Construct

<400> SEQUENCE: 68

Met Glu Arg Thr Val Ile Ala Leu Ala Ile Ile Ser Val Val Lys Gly
1               5                   10                  15

<210> SEQ ID NO 69
<211> LENGTH: 7
<212> TYPE: PRT
<213> ORGANISM: Artificial Sequence
<220> FEATURE:
<223> OTHER INFORMATION: Synthetic Construct

<400> SEQUENCE: 69

Met Val Val Thr Ser Asn Ala
1               5

<210> SEQ ID NO 70
<211> LENGTH: 16
<212> TYPE: PRT
<213> ORGANISM: Artificial Sequence
<220> FEATURE:
<223> OTHER INFORMATION: Synthetic Construct

<400> SEQUENCE: 70

Met Lys Lys Ile Val Leu Leu Leu Ala Ile Val Ser Leu Val Lys Ser
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Synthetic Construct

<400> SEQUENCE: 71

Met Lys Thr Val Ile Ala Leu Ser Tyr Ile Leu Cys Leu Thr Phe Gly

<210> SEQ ID NO 72
<211> LENGTH: 16
<212> TYPE: PRT
<213> ORGANISM: Artificial Sequence
<220> FEATURE:
<223> OTHER INFORMATION: Synthetic Construct

<400> SEQUENCE: 72

Met Glu Arg Ile Val Leu Phe Leu Ala Ile Val Ser Leu Val Lys Ser
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Synthetic Construct

<400> SEQUENCE: 73

Met Lys Thr Ile Ile Val Leu Ser Tyr Phe Phe Cys Leu Ala Leu Ser
1               5                   10                  15

<210> SEQ ID NO 74
<211> LENGTH: 17
<212> TYPE: PRT
<213> ORGANISM: Artificial Sequence
<220> FEATURE:
<223> OTHER INFORMATION: Synthetic Construct

<400> SEQUENCE: 74

Met Tyr Lys Val Val Ile Ile Ala Leu Leu Gly Ala Val Lys Gly
1               5                   10                  15

Leu

<210> SEQ ID NO 75
<211> LENGTH: 14
<212> TYPE: PRT
<213> ORGANISM: Artificial Sequence
<220> FEATURE:
<223> OTHER INFORMATION: Synthetic Construct

<400> SEQUENCE: 75

Lys Ile Val Leu Leu Leu Ala Ile Val Ser Leu Val Lys Ser
1               5                   10

<210> SEQ ID NO 76
<211> LENGTH: 18
<212> TYPE: PRT
<213> ORGANISM: Artificial Sequence
<220> FEATURE:
<223> OTHER INFORMATION: Synthetic Construct

<400> SEQUENCE: 76

Met Asn Thr Gln Ile Leu Ile Leu Ala Thr Ser Ala Phe Phe Tyr Val
1               5                   10                  15

Arg Ala

<210> SEQ ID NO 77
<211> LENGTH: 16
<212> TYPE: PRT
<213> ORGANISM: Artificial Sequence
<220> FEATURE:
<223> OTHER INFORMATION: Synthetic Construct

```
<400> SEQUENCE: 77

Met Glu Arg Val Val Leu Leu Leu Ala Met Ile Ser Leu Val Lys Ser
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Synthetic Construct

<400> SEQUENCE: 78

Met Lys Thr Leu Ile Ala Leu Ser Tyr Ile Phe Cys Leu Val Leu Gly
1               5                   10                  15

<210> SEQ ID NO 79
<211> LENGTH: 18
<212> TYPE: PRT
<213> ORGANISM: Artificial Sequence
<220> FEATURE:
<223> OTHER INFORMATION: Synthetic Construct

<400> SEQUENCE: 79

Met Asn Thr Gln Ile Leu Val Phe Ala Leu Val Ala Val Ile His Thr
1               5                   10                  15

Asn Ala

<210> SEQ ID NO 80
<211> LENGTH: 16
<212> TYPE: PRT
<213> ORGANISM: Artificial Sequence
<220> FEATURE:
<223> OTHER INFORMATION: Synthetic Construct

<400> SEQUENCE: 80

Met Ile Ala Ile Ile Val Val Ala Ile Leu Ala Thr Ala Gly Arg Ser
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Synthetic Construct

<400> SEQUENCE: 81

Met Glu Lys Ile Val Leu Leu Phe Ala Ile Val Ser Leu Val Arg Ser
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Synthetic Construct

<400> SEQUENCE: 82

Met Glu Lys Thr Val Leu Leu Leu Ala Thr Val Ser Leu Val Lys Ser
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Synthetic Construct
```

<400> SEQUENCE: 83

Met Glu Arg Ile Val Leu Leu Leu Ala Ile Val Ser Leu Val Lys Ser
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Synthetic Construct

<400> SEQUENCE: 84

Met Leu Ser Val Val Ile Leu Phe Leu Leu Val Ala Glu Asn Ser Ser
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Synthetic Construct

<400> SEQUENCE: 85

Met Lys Lys Ile Leu Leu Phe Thr Val Ile Phe Leu Tyr Ala Lys Ala
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Synthetic Construct

<400> SEQUENCE: 86

Met Glu Lys Leu Leu Leu Phe Ala Thr Ile Ile Leu Cys Val Lys Ala
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Synthetic Construct

<400> SEQUENCE: 87

Met Leu Ser Ile Val Val Leu Leu Leu Ile Ala Glu Ser Ser Ser
1               5                   10                  15

<210> SEQ ID NO 88
<211> LENGTH: 17
<212> TYPE: PRT
<213> ORGANISM: Artificial Sequence
<220> FEATURE:
<223> OTHER INFORMATION: Synthetic Construct

<400> SEQUENCE: 88

Met Glu Ala Lys Leu Phe Val Leu Phe Cys Ala Phe Thr Thr Leu Glu
1               5                   10                  15

Ala

<210> SEQ ID NO 89
<211> LENGTH: 16
<212> TYPE: PRT
<213> ORGANISM: Artificial Sequence
<220> FEATURE:

```
<223> OTHER INFORMATION: Synthetic Construct

<400> SEQUENCE: 89

Met Lys Thr Ile Ile Ala Leu Ser His Ile Phe Cys Leu Val Leu Gly
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Synthetic Construct

<400> SEQUENCE: 90

Met Leu Ser Ile Val Val Leu Leu Leu Met Ala Glu Gly Ser Ser
1               5                   10                  15

<210> SEQ ID NO 91
<211> LENGTH: 17
<212> TYPE: PRT
<213> ORGANISM: Artificial Sequence
<220> FEATURE:
<223> OTHER INFORMATION: Synthetic Construct

<400> SEQUENCE: 91

Met Ile Ala Leu Ile Leu Val Ala Leu Ala Leu Ser His Thr Ala Tyr
1               5                   10                  15

Ser

<210> SEQ ID NO 92
<211> LENGTH: 17
<212> TYPE: PRT
<213> ORGANISM: Artificial Sequence
<220> FEATURE:
<223> OTHER INFORMATION: Synthetic Construct

<400> SEQUENCE: 92

Met Lys Ala Ile Leu Leu Val Leu Leu Tyr Thr Phe Thr Ala Ala Asn
1               5                   10                  15

Ala

<210> SEQ ID NO 93
<211> LENGTH: 17
<212> TYPE: PRT
<213> ORGANISM: Artificial Sequence
<220> FEATURE:
<223> OTHER INFORMATION: Synthetic Construct

<400> SEQUENCE: 93

Met Lys Ala Asn Leu Leu Val Leu Leu Cys Ala Leu Ala Ala Ala Asp
1               5                   10                  15

Ala

<210> SEQ ID NO 94
<211> LENGTH: 17
<212> TYPE: PRT
<213> ORGANISM: Artificial Sequence
<220> FEATURE:
<223> OTHER INFORMATION: Synthetic Construct

<400> SEQUENCE: 94

Met Lys Ala Ile Leu Leu Val Leu Leu Cys Thr Phe Ala Ala Thr Asn
1               5                   10                  15

Ala
```

<210> SEQ ID NO 95
<211> LENGTH: 17
<212> TYPE: PRT
<213> ORGANISM: Artificial Sequence
<220> FEATURE:
<223> OTHER INFORMATION: Synthetic Construct

<400> SEQUENCE: 95

Met Lys Ala Lys Leu Leu Ile Leu Phe Cys Ala Phe Thr Ala Thr Asp
1               5                   10                  15

Ala

<210> SEQ ID NO 96
<211> LENGTH: 16
<212> TYPE: PRT
<213> ORGANISM: Artificial Sequence
<220> FEATURE:
<223> OTHER INFORMATION: Synthetic Construct

<400> SEQUENCE: 96

Met Glu Lys Ile Val Leu Leu Phe Ala Ile Val Ser Leu Val Lys Ser
1               5                   10                  15

<210> SEQ ID NO 97
<211> LENGTH: 18
<212> TYPE: PRT
<213> ORGANISM: Artificial Sequence
<220> FEATURE:
<223> OTHER INFORMATION: Synthetic Construct

<400> SEQUENCE: 97

Met Glu Thr Lys Ala Ile Ile Ala Ala Leu Leu Met Val Thr Ala Ala
1               5                   10                  15

Asn Ala

<210> SEQ ID NO 98
<211> LENGTH: 16
<212> TYPE: PRT
<213> ORGANISM: Artificial Sequence
<220> FEATURE:
<223> OTHER INFORMATION: Synthetic Construct

<400> SEQUENCE: 98

Met Leu Ser Ile Thr Ile Leu Phe Leu Leu Ile Ala Glu Val Ser Ser
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Synthetic Construct

<400> SEQUENCE: 99

Met Lys Thr Ile Ile Ala Leu Ser Tyr Ile Phe Cys Gln Val Leu Ala
1               5                   10                  15

<210> SEQ ID NO 100
<211> LENGTH: 17
<212> TYPE: PRT
<213> ORGANISM: Artificial Sequence
<220> FEATURE:
<223> OTHER INFORMATION: Synthetic Construct

<400> SEQUENCE: 100

```
Met Lys Ala Lys Leu Leu Val Leu Phe Cys Ala Phe Thr Ala Thr Asp
1               5                   10                  15

Ala

<210> SEQ ID NO 101
<211> LENGTH: 5
<212> TYPE: PRT
<213> ORGANISM: Artificial Sequence
<220> FEATURE:
<223> OTHER INFORMATION: Synthetic Construct

<400> SEQUENCE: 101

Val Thr Ser Asn Ala
1               5

<210> SEQ ID NO 102
<211> LENGTH: 17
<212> TYPE: PRT
<213> ORGANISM: Artificial Sequence
<220> FEATURE:
<223> OTHER INFORMATION: Synthetic Construct

<400> SEQUENCE: 102

Met Tyr Lys Val Val Val Ile Ile Ala Leu Leu Gly Ala Val Arg Gly
1               5                   10                  15

Leu

<210> SEQ ID NO 103
<211> LENGTH: 12
<212> TYPE: PRT
<213> ORGANISM: Artificial Sequence
<220> FEATURE:
<223> OTHER INFORMATION: Synthetic Construct

<400> SEQUENCE: 103

Leu Val Ala Leu Ala Leu Ser Gln Thr Ala Tyr Ser
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Synthetic Construct

<400> SEQUENCE: 104

Ile Ile Val Leu Leu Met Val Val Thr Ser Asn Ala
1               5                   10

<210> SEQ ID NO 105
<211> LENGTH: 17
<212> TYPE: PRT
<213> ORGANISM: Artificial Sequence
<220> FEATURE:
<223> OTHER INFORMATION: Synthetic Construct

<400> SEQUENCE: 105

Met Tyr Lys Ile Val Leu Val Leu Thr Leu Phe Gly Ala Val Asn Gly
1               5                   10                  15

Leu

<210> SEQ ID NO 106
<211> LENGTH: 18
<212> TYPE: PRT
```

<213> ORGANISM: Artificial Sequence
<220> FEATURE:
<223> OTHER INFORMATION: Synthetic Construct

<400> SEQUENCE: 106

Met Asn Thr Gln Ile Leu Val Phe Ile Ala Cys Val Leu Ile Lys Ala
1               5                   10                  15

Lys Gly

<210> SEQ ID NO 107
<211> LENGTH: 16
<212> TYPE: PRT
<213> ORGANISM: Artificial Sequence
<220> FEATURE:
<223> OTHER INFORMATION: Synthetic Construct

<400> SEQUENCE: 107

Met Lys Thr Ile Ile Ala Leu Ser Tyr Ile Leu Cys Leu Val Phe Ala
1               5                   10                  15

<210> SEQ ID NO 108
<211> LENGTH: 18
<212> TYPE: PRT
<213> ORGANISM: Artificial Sequence
<220> FEATURE:
<223> OTHER INFORMATION: Synthetic Construct

<400> SEQUENCE: 108

Met Phe Leu Leu Pro Arg Phe Val Leu Val Ser Cys Ile Ile Gly Ser
1               5                   10                  15

Leu Gly

<210> SEQ ID NO 109
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(15)
<223> OTHER INFORMATION: Xaa can be any naturally occurring amino acid

<400> SEQUENCE: 109

Met Cys Ile Ala Met Ala Pro Arg Thr Leu Leu Leu Leu Ile Xaa Cys
1               5                   10                  15

Gln Leu Val Phe
            20

<210> SEQ ID NO 110
<211> LENGTH: 18
<212> TYPE: PRT
<213> ORGANISM: Artificial Sequence
<220> FEATURE:
<223> OTHER INFORMATION: Synthetic Construct

<400> SEQUENCE: 110

Met Phe Leu Leu Leu Arg Phe Val Leu Val Ser Cys Ile Ile Gly Ser
1               5                   10                  15

Leu Gly

<210> SEQ ID NO 111
<211> LENGTH: 24
<212> TYPE: PRT
<213> ORGANISM: Artificial Sequence
<220> FEATURE:
<223> OTHER INFORMATION: Synthetic Construct

<400> SEQUENCE: 111

Met Gly Ser Met Cys Ile Ala Met Ala Pro Arg Thr Leu Leu Leu Leu
1               5                   10                  15

Ile Gly Cys Gln Leu Ala Leu Gly
            20

<210> SEQ ID NO 112
<211> LENGTH: 14
<212> TYPE: PRT
<213> ORGANISM: Artificial Sequence
<220> FEATURE:
<223> OTHER INFORMATION: Synthetic Construct

<400> SEQUENCE: 112

Met Leu Ser Leu Ile Leu Phe Phe Pro Ser Phe Ala Phe Ala
1               5                   10

<210> SEQ ID NO 113
<211> LENGTH: 18
<212> TYPE: PRT
<213> ORGANISM: Artificial Sequence
<220> FEATURE:
<223> OTHER INFORMATION: Synthetic Construct

<400> SEQUENCE: 113

Met Phe Leu Leu Pro Arg Phe Ile Leu Val Ser Cys Ile Ile Gly Ser
1               5                   10                  15

Leu Gly

<210> SEQ ID NO 114
<211> LENGTH: 13
<212> TYPE: PRT
<213> ORGANISM: Artificial Sequence
<220> FEATURE:
<223> OTHER INFORMATION: Synthetic Construct

<400> SEQUENCE: 114

Met Leu Ile Ile Phe Leu Phe Phe Asn Phe Cys Tyr Gly
1               5                   10

<210> SEQ ID NO 115
<211> LENGTH: 24
<212> TYPE: PRT
<213> ORGANISM: Artificial Sequence
<220> FEATURE:
<223> OTHER INFORMATION: Synthetic Construct

<400> SEQUENCE: 115

Met Gly Arg Met Cys Ile Ala Met Ala Pro Arg Thr Leu Leu Leu Leu
1               5                   10                  15

Ile Gly Cys Gln Leu Val Phe Gly
            20

<210> SEQ ID NO 116
<211> LENGTH: 27
<212> TYPE: PRT
<213> ORGANISM: Artificial Sequence
<220> FEATURE:
<223> OTHER INFORMATION: Synthetic Construct

<400> SEQUENCE: 116

Met Leu Arg Met Arg Val Arg Pro Pro Ser Ala Ile Pro Val Phe Leu
1               5                   10                  15

```
1               5                   10                  15

Ile Phe Val Leu Leu Pro Phe Val Leu Thr Ser
            20                  25
```

<210> SEQ ID NO 117
<211> LENGTH: 13
<212> TYPE: PRT
<213> ORGANISM: Artificial Sequence
<220> FEATURE:
<223> OTHER INFORMATION: Synthetic Construct

<400> SEQUENCE: 117

```
Met Leu Ile Ile Phe Leu Phe Phe Tyr Phe Cys Tyr Gly
1               5                   10
```

<210> SEQ ID NO 118
<211> LENGTH: 19
<212> TYPE: PRT
<213> ORGANISM: Artificial Sequence
<220> FEATURE:
<223> OTHER INFORMATION: Synthetic Construct

<400> SEQUENCE: 118

```
Met Cys Ile Ala Met Ala Pro Arg Thr Leu Leu Leu Ile Gly Cys
1               5                   10                  15

Gln Leu Val
```

<210> SEQ ID NO 119
<211> LENGTH: 23
<212> TYPE: PRT
<213> ORGANISM: Artificial Sequence
<220> FEATURE:
<223> OTHER INFORMATION: Synthetic Construct

<400> SEQUENCE: 119

```
Met Ala Arg Thr Asp Ala Met Ala Pro Arg Thr Leu Leu Val Leu
1               5                   10                  15

Ser Leu Gly Tyr Ala Phe Gly
            20
```

<210> SEQ ID NO 120
<211> LENGTH: 18
<212> TYPE: PRT
<213> ORGANISM: Artificial Sequence
<220> FEATURE:
<223> OTHER INFORMATION: Synthetic Construct

<400> SEQUENCE: 120

```
Met Phe Leu Leu Pro Arg Phe Cys Leu Val Cys Ser Ile Ile Ser Thr
1               5                   10                  15

Phe Gly
```

<210> SEQ ID NO 121
<211> LENGTH: 22
<212> TYPE: PRT
<213> ORGANISM: Artificial Sequence
<220> FEATURE:
<223> OTHER INFORMATION: Synthetic Construct

<400> SEQUENCE: 121

```
Met Gly Ser Thr Cys Ile Ala Met Ala Pro Arg Thr Leu Leu Leu
1               5                   10                  15

Ile Gly Cys Gln Leu Val
            20
```

```
<210> SEQ ID NO 122
<211> LENGTH: 18
<212> TYPE: PRT
<213> ORGANISM: Artificial Sequence
<220> FEATURE:
<223> OTHER INFORMATION: Synthetic Construct

<400> SEQUENCE: 122

Met Phe Leu Leu Pro Arg Phe Cys Leu Val Cys Ser Ile Ile Gly Thr
1               5                   10                  15

Phe Gly

<210> SEQ ID NO 123
<211> LENGTH: 14
<212> TYPE: PRT
<213> ORGANISM: Artificial Sequence
<220> FEATURE:
<223> OTHER INFORMATION: Synthetic Construct

<400> SEQUENCE: 123

Met Phe Phe Ser Leu Leu Leu Met Leu Gly Leu Thr Glu Ala
1               5                   10

<210> SEQ ID NO 124
<211> LENGTH: 14
<212> TYPE: PRT
<213> ORGANISM: Artificial Sequence
<220> FEATURE:
<223> OTHER INFORMATION: Synthetic Construct

<400> SEQUENCE: 124

Met Phe Phe Ser Leu Leu Leu Val Leu Gly Leu Thr Glu Ala
1               5                   10

<210> SEQ ID NO 125
<211> LENGTH: 7
<212> TYPE: PRT
<213> ORGANISM: Artificial Sequence
<220> FEATURE:
<223> OTHER INFORMATION: Synthetic Construct

<400> SEQUENCE: 125

Met Leu Gly Leu Thr Glu Ala
1               5
```